(12) United States Patent
Forsell

(10) Patent No.: US 11,207,186 B2
(45) Date of Patent: *Dec. 28, 2021

(54) HIP JOINT DEVICE AND METHOD

(71) Applicant: Peter Forsell, Bouveret (CH)

(72) Inventor: Peter Forsell, Bouveret (CH)

( * ) Notice: Subject to any disclaimer, the term of this patent is extended or adjusted under 35 U.S.C. 154(b) by 239 days.

This patent is subject to a terminal disclaimer.

(21) Appl. No.: 15/978,273

(22) Filed: May 14, 2018

(65) Prior Publication Data

US 2018/0256344 A1 Sep. 13, 2018

Related U.S. Application Data

(63) Continuation of application No. 14/935,467, filed on Nov. 9, 2015, now Pat. No. 9,968,457, which is a continuation of application No. 13/383,263, filed as application No. PCT/SE2010/050807 on Jul. 12, 2010, now Pat. No. 9,180,014.

(Continued)

(30) Foreign Application Priority Data

| Jul. 10, 2009 | (SE) | 0900957-2 |
|---|---|---|
| Jul. 10, 2009 | (SE) | 0900958-0 |
| Jul. 10, 2009 | (SE) | 0900959-8 |
| Jul. 10, 2009 | (SE) | 0900960-6 |
| Jul. 10, 2009 | (SE) | 0900962-2 |
| Jul. 10, 2009 | (SE) | 0900963-0 |

(Continued)

(51) Int. Cl.
*A61F 2/32* (2006.01)
*A61F 2/34* (2006.01)

(Continued)

(52) U.S. Cl.
CPC ........ *A61F 2/3607* (2013.01); *A61B 17/1617* (2013.01); *A61B 17/1631* (2013.01);
(Continued)

(58) Field of Classification Search
CPC ...... A61F 2/32; A61F 2/34; A61F 2/36; A61F 2/40; A61F 2/4081; A61F 2/4014;
(Continued)

(56) References Cited

U.S. PATENT DOCUMENTS 6,010,535 A * 1/2000 Shah ........................ A61F 2/32
623/22.16

* cited by examiner

*Primary Examiner* — Brian A Dukert

(57) ABSTRACT

A medical device for implantation in a hip joint of a human patient, the natural hip joint having a ball shaped caput femur as the proximal part of the femoral bone with a convex hip joint surface towards the center of the hip joint and a bowl shaped acetabulum as part of the pelvic bone with a concave hip joint surface towards the center of the hip joint. The medical device comprising; an artificial caput femur, comprising a convex surface towards the center of the hip joint. The artificial convex caput femur is adapted to, when implanted: be fixated to the pelvic bone of the human patient, and be in movable connection with an artificial acetabulum surface fixated to the femoral bone of the patient, thereby forming a ball and socket joint. The medical device further comprises a fixation element comprising a fixation surface adapted to be in contact with the surface of the acetabulum and adapted to fixate the artificial convex caput femur to at least the acetabulum of the pelvic bone.

16 Claims, 21 Drawing Sheets

Related U.S. Application Data

(60) Provisional application No. 61/229,739, filed on Jul. 30, 2009, provisional application No. 61/229,743, filed on Jul. 30, 2009, provisional application No. 61/229,745, filed on Jul. 30, 2009, provisional application No. 61/229,746, filed on Jul. 30, 2009, provisional application No. 61/229,747, filed on Jul. 30, 2009, provisional application No. 61/229,748, filed on Jul. 30, 2009, provisional application No. 61/229,751, filed on Jul. 30, 2009, provisional application No. 61/229,752, filed on Jul. 30, 2009, provisional application No. 61/229,755, filed on Jul. 30, 2009, provisional application No. 61/229,761, filed on Jul. 30, 2009, provisional application No. 61/229,767, filed on Jul. 30, 2009, provisional application No. 61/229,778, filed on Jul. 30, 2009, provisional application No. 61/229,786, filed on Jul. 30, 2009, provisional application No. 61/229,796, filed on Jul. 30, 2009, provisional application No. 61/229,735, filed on Jul. 30, 2009, provisional application No. 61/229,789, filed on Jul. 30, 2009, provisional application No. 61/229,738, filed on Jul. 30, 2009.

(30) Foreign Application Priority Data

| Jul. 10, 2009 | (SE) | 0900965-5 |
| Jul. 10, 2009 | (SE) | 0900966-3 |
| Jul. 10, 2009 | (SE) | 0900968-9 |
| Jul. 10, 2009 | (SE) | 0900969-7 |
| Jul. 10, 2009 | (SE) | 0900970-5 |
| Jul. 10, 2009 | (SE) | 0900972-1 |
| Jul. 10, 2009 | (SE) | 0900973-9 |
| Jul. 10, 2009 | (SE) | 0900974-7 |
| Jul. 10, 2009 | (SE) | 0900976-2 |
| Jul. 10, 2009 | (SE) | 0900978-8 |
| Jul. 10, 2009 | (SE) | 0900981-2 |

(51) Int. Cl.

| *A61F 2/36* | (2006.01) |
| *A61B 17/16* | (2006.01) |
| *A61F 2/30* | (2006.01) |
| *A61B 17/56* | (2006.01) |
| *A61L 27/26* | (2006.01) |
| *A61F 2/28* | (2006.01) |
| *A61L 27/20* | (2006.01) |
| *A61L 27/50* | (2006.01) |
| *A61B 17/74* | (2006.01) |
| *A61B 17/86* | (2006.01) |
| *A61F 2/46* | (2006.01) |
| *A61F 2/48* | (2006.01) |
| *A61B 17/00* | (2006.01) |
| *A61B 17/68* | (2006.01) |
| *A61B 17/88* | (2006.01) |
| *A61B 17/02* | (2006.01) |
| *A61B 17/84* | (2006.01) |

(52) U.S. Cl.
CPC ...... *A61B 17/1637* (2013.01); *A61B 17/1666* (2013.01); *A61B 17/1668* (2013.01); *A61B 17/56* (2013.01); *A61B 17/562* (2013.01); *A61F 2/28* (2013.01); *A61F 2/30721* (2013.01); *A61F 2/30724* (2013.01); *A61F 2/30734* (2013.01); *A61F 2/30756* (2013.01); *A61F 2/32* (2013.01); *A61F 2/34* (2013.01); *A61F 2/36* (2013.01); *A61F 2/3601* (2013.01); *A61F 2/3603* (2013.01); *A61F 2/3609* (2013.01); *A61F 2/3662* (2013.01); *A61L 27/20* (2013.01); *A61L 27/26* (2013.01); *A61L 27/50* (2013.01); *A61B 17/00234* (2013.01); *A61B 17/00491* (2013.01); *A61B 17/1604* (2013.01); *A61B 17/1664* (2013.01); *A61B 17/686* (2013.01); *A61B 17/74* (2013.01); *A61B 17/84* (2013.01); *A61B 17/86* (2013.01); *A61B 17/8872* (2013.01); *A61B 2017/0275* (2013.01); *A61F 2/30749* (2013.01); *A61F 2/4607* (2013.01); *A61F 2/4609* (2013.01); *A61F 2/4637* (2013.01); *A61F 2002/302* (2013.01); *A61F 2002/305* (2013.01); *A61F 2002/30014* (2013.01); *A61F 2002/30062* (2013.01); *A61F 2002/3067* (2013.01); *A61F 2002/30069* (2013.01); *A61F 2002/3085* (2013.01); *A61F 2002/30125* (2013.01); *A61F 2002/30153* (2013.01); *A61F 2002/30154* (2013.01); *A61F 2002/30166* (2013.01); *A61F 2002/30179* (2013.01); *A61F 2002/30205* (2013.01); *A61F 2002/30364* (2013.01); *A61F 2002/30383* (2013.01); *A61F 2002/30387* (2013.01); *A61F 2002/30405* (2013.01); *A61F 2002/30462* (2013.01); *A61F 2002/30469* (2013.01); *A61F 2002/30471* (2013.01); *A61F 2002/30495* (2013.01); *A61F 2002/30507* (2013.01); *A61F 2002/30558* (2013.01); *A61F 2002/30563* (2013.01); *A61F 2002/30565* (2013.01); *A61F 2002/30566* (2013.01); *A61F 2002/30576* (2013.01); *A61F 2002/30578* (2013.01); *A61F 2002/30579* (2013.01); *A61F 2002/30583* (2013.01); *A61F 2002/30589* (2013.01); *A61F 2002/30594* (2013.01); *A61F 2002/30601* (2013.01); *A61F 2002/30604* (2013.01); *A61F 2002/30616* (2013.01); *A61F 2002/30668* (2013.01); *A61F 2002/30673* (2013.01); *A61F 2002/30675* (2013.01); *A61F 2002/30726* (2013.01); *A61F 2002/30729* (2013.01); *A61F 2002/30733* (2013.01); *A61F 2002/30736* (2013.01); *A61F 2002/30754* (2013.01); *A61F 2002/30757* (2013.01); *A61F 2002/30759* (2013.01); *A61F 2002/30841* (2013.01); *A61F 2002/30878* (2013.01); *A61F 2002/30886* (2013.01); *A61F 2002/30922* (2013.01); *A61F 2002/30968* (2013.01); *A61F 2002/3208* (2013.01); *A61F 2002/3233* (2013.01); *A61F 2002/3241* (2013.01); *A61F 2002/342* (2013.01); *A61F 2002/3443* (2013.01); *A61F 2002/3483* (2013.01); *A61F 2002/3487* (2013.01); *A61F 2002/3493* (2013.01); *A61F 2002/3495* (2013.01); *A61F 2002/365* (2013.01); *A61F 2002/3615* (2013.01); *A61F 2002/3625* (2013.01); *A61F 2002/3631* (2013.01); *A61F 2002/3686* (2013.01); *A61F 2002/4631* (2013.01); *A61F 2002/4635* (2013.01); *A61F 2002/4655* (2013.01); *A61F 2002/4677* (2013.01); *A61F 2002/482* (2013.01); *A61F 2002/485* (2013.01); *A61F 2240/002* (2013.01); *A61L 2400/10* (2013.01)

(58) Field of Classification Search
CPC .... A61F 2/3607; A61F 2/3609; A61B 17/844; A61B 17/846
See application file for complete search history.

A - A

B - B

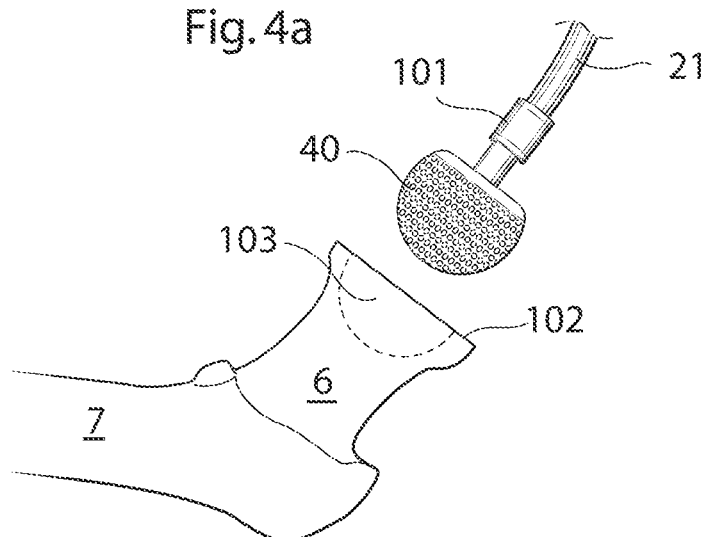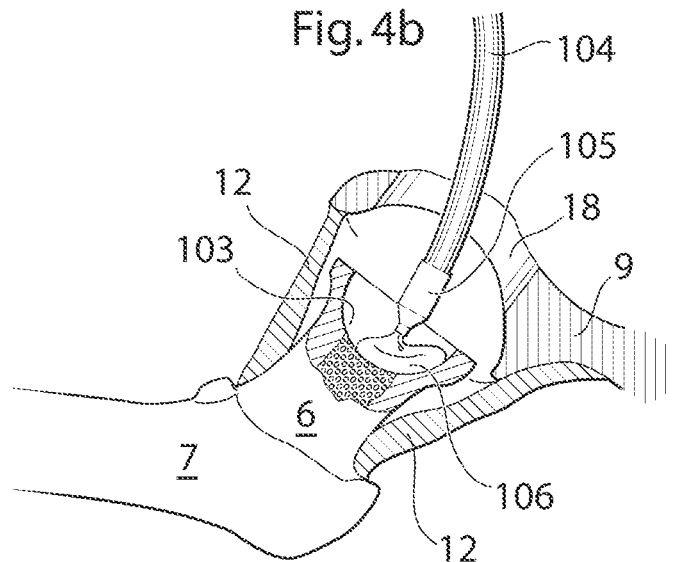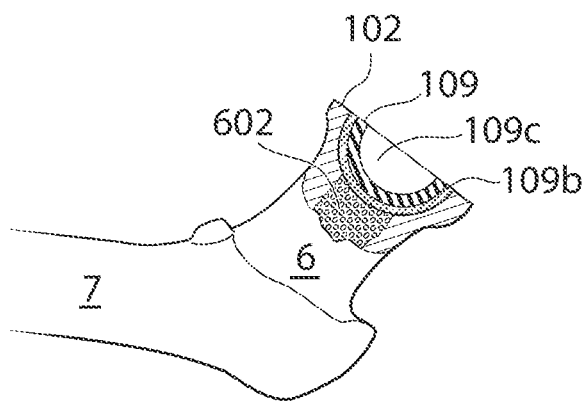

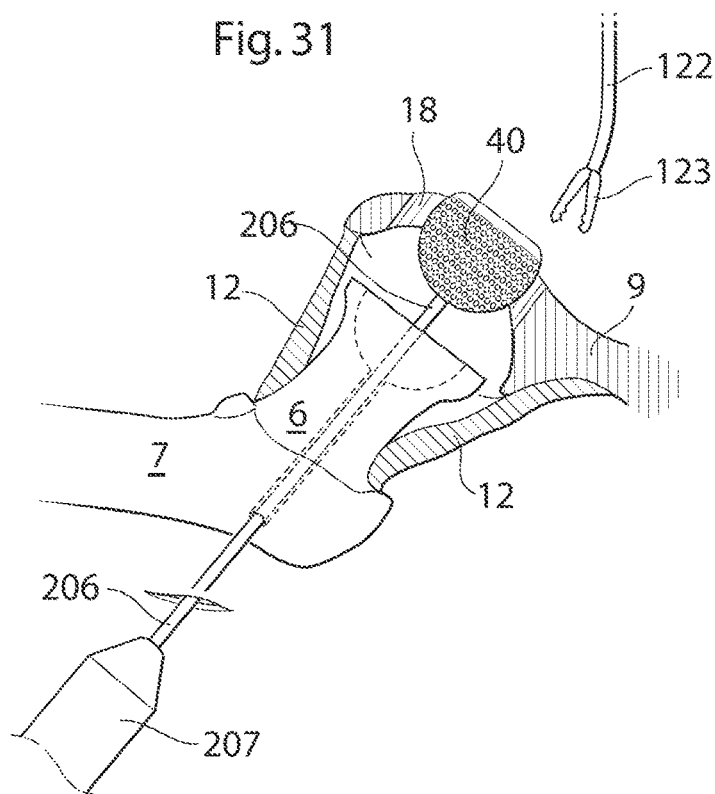
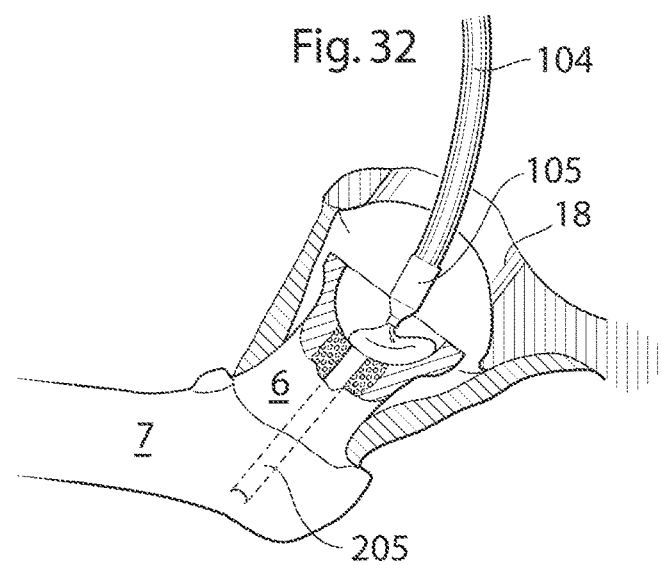
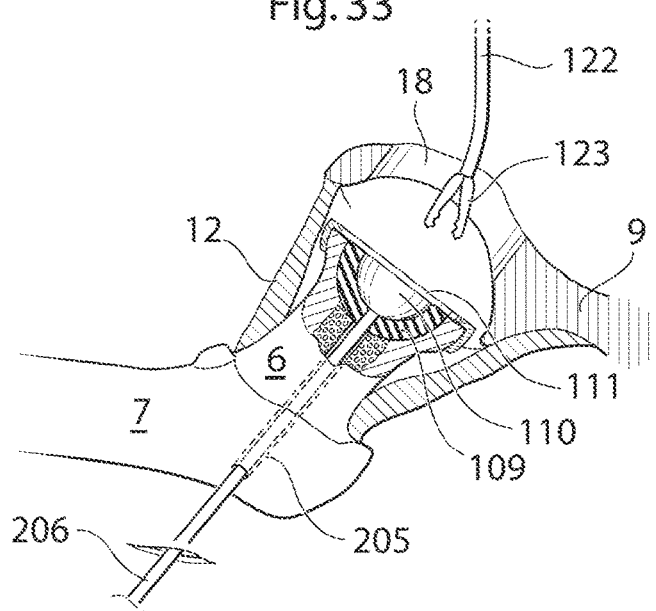

HIP JOINT DEVICE AND METHOD

This application is a continuation of U.S. application Ser. No. 14/935,467 filed on Nov. 9, 2015, which is a continuation of U.S. application Ser. No. 13/383,263 filed Jan. 10, 2012 and issued on Nov. 10, 2015 as U.S. Pat. No. 9,180,014, which is the U.S. national phase of International Application No. PCT/SE2010/050807, filed Jul. 12, 2010, which designated the U.S. and claims the benefit of U.S. Provisional Applications Nos. 61/229,739, 61/229,743, 61/229,745, 61/229,746, 61/229,747, 61/229,748, 61/229,751, 61/229,752, 61/229,755, 61/229,761, 61/229,767, 61/229,778, 61/229,786, 61/229,796, 61/229,735, 61/229,789, 61/229,738, all filed Jul. 30, 2009, and Priority from Swedish patent applications No. 0900981-2, 0900957-2, 0900959-8, 0900960-6, 0900962-2, 0900963-0, 0900965-5, 0900966-3, 0900968-9, 0900969-7, 0900970-5, 0900972-1, 0900973-9, 0900974-7, 0900976-2, 0900978-8, 0900958-0, all filed Jul. 10, 2009, the entire contents of each of which is hereby incorporated by reference in this application.

FIELD OF INVENTION

The present invention relates generally to a medical device for implantation in a hip joint, and a method of providing said medical device.

BACKGROUND

Hip joint Osteoarthritis is a syndrome in which low-grade inflammation results in pain in the hip joints, caused by abnormal wearing of the Cartilage that acts as a cushion inside if the hip joint. This abnormal wearing of the cartilage also results in a decrease of the joints lubricating fluid called Synovial fluid. Hip joint Osteoarthritis is estimated to affect 80% of all people over 65 years of age, in more or less serious forms.

The present treatment for hip osteoarthritis comprises NSAID drugs, local injections of Hyaluronic acid or Glucocorticoid to help lubricating the hip joint, and replacing parts of the hip joint with a prosthesis through hip joint surgery.

The replacing of parts of the hip joint is one of the most common surgeries to date performed at hundreds of thousands of patients in the world every year. The most common method comprises placing a metal prosthesis in Femur and a plastic bowl in Acetabulum. This operation is usually done through a lateral incision in the hip and upper thigh and through, Fascia Lata and the lateral muscles of the thigh. To get access to the hip joint, the supporting hip joint capsule attached to Femur and Ilium of Pelvis needs to be penetrated, making it difficult to get a fully functional joint after the surgery. Femur is then cut at the neck with a bone saw and the prosthesis is placed in femur either with bone cement or without. Acetabulum is slightly enlarged using an Acetabular reamer, and the plastic bowl is positioned using screws or bone cement.

The surgery typically requires one week of hospitalization due to the increased risk of infection. The recovery process is on average about 6 weeks, but even after this period the patient should not perform any physical activates that places large strain on the joint.

SUMMARY

A medical device for treating hip joint osteoarthritis in a human patient by providing at least one artificial hip joint surface is provided. The hip joint having a ball shaped caput femur as the proximal part of the femoral bone with a convex hip joint surface towards the centre of the hip joint and a bowl shaped acetabulum as part of the pelvic bone with a concave hip joint surface towards the centre of the hip joint. The medical device comprising the artificial hip joint surface comprises at least one of; an artificial caput femur or an artificial caput femur surface comprising, a convex form towards the centre of the hip joint, and an artificial acetabulum or an artificial acetabulum surface comprising, a concave form towards the centre of the hip joint. The artificial convex caput femur or the artificial convex caput femur surface is adapted to be fixated to the pelvic bone of the human patient, and the artificial concave acetabulum or artificial concave acetabulum surface is adapted to be fixated to the femoral bone of the human patient.

Alternatively a medical device for treating hip joint osteoarthritis by providing at least one joint surface is provided. The hip joint has a ball shaped caput femur as the proximal part of the femoral bone with a convex hip joint surface and a bowl shaped acetabulum as part of the pelvic bone with a concave hip joint surface.

The medical device could comprise an artificial convex hip joint surface adapted to replace the convex hip joint surface. The artificial convex hip joint surface could be adapted to be fixated to the pelvic bone of the human patient.

According to one embodiment, the medical device comprises an artificial convex hip joint surface adapted to be inserted through a hole in the pelvic bone of the human patient.

According to one embodiment, the medical device comprises an artificial convex hip joint surface adapted to be inserted through a hole in the hip joint capsule of the human patient.

According to one embodiment, the medical device comprises an artificial convex hip joint surface adapted to be inserted through a hole in the femoral bone of the human patient.

The medical device could be adapted to be placed in an artificial replacement of the concave acetabulum hip joint surface. The artificial replacement could be adapted to be fixated to the caput femur, the collum femur or the femoral bone.

According to one embodiment the artificial convex hip joint surface in the medical device comprises at least two artificial hip joint surface parts adapted to be placed in connection with each other after the insertion in the human patient. The at least two artificial hip joint surface parts could be adapted to be inserted through a hole in the pelvic bone from the opposite side from acetabulum of the human patient, said hole having a diameter less than the largest diameter of said medical device. It is also conceivable that the at least two artificial hip joint surface parts are adapted to be inserted through a hole in the femoral bone or the hip joint capsule of the human patient. The hole having a diameter smaller than the largest diameter of the medical device.

According to any of the embodiments above, at least one of said at least two artificial hip joint surface parts could be adapted to serve as base part to which at least one additional artificial caput femur surface part can be connected.

The connection of said at least two artificial hip joint surface parts could be performed using at least one of: at least one screw, at least one pin, at least one portion of at least one of the parts adapted to be introduced into the other part, the parts being adapted to be sliding into the other part, form fitting, welding, adhesive, pin, wire, a ball mounted into a bowl being portions of said parts, a male portion of one part mounted into a female portion of the other part, a key introduced into a lock being portions of said parts, band, or other mechanical connecting members. It is also conceivable that the at least two artificial hip joint surface parts are adapted to mechanically connect to each other using self locking members, in which case the self locking members could be assisted by adhesive or bone cement.

According to one embodiment, the medical device comprises at least one elastic member. The at least one elastic member could be adapted for changing the largest diameter or largest cross-sectional distance of the medical device for insertion through a hole having a diameter smaller than said largest diameter or cross-sectional distance of said medical device.

Fixation

To fixate the medical device it is conceivable that the medical device comprises a fixation support to anchor the artificial convex hip joint surface. The fixation support is adapted to anchor the artificial convex hip joint surface to the pelvic bone, to support at least part of the load applied to the hip joint in normal use.

According to one embodiment the fixation support comprises a displaceable part or section. The displaceable part or section could be adapted to carry the load applied to the hip joint in normal use.

According to one embodiment the medical device could be adapted to be fixated to the pelvic bone using at least one of: at least one screw, at least one pin, at least one portion of at least one of the parts adapted to be introduced into the other part, the parts being adapted to be sliding into the other part, form fitting, welding, adhesive, pin, wire, a ball mounted into a bowl being portions of said parts, a male portion of one part mounted into a female portion of the other part, a key introduced into a lock being portions of said parts, band, or other mechanical connecting members.

According to one embodiment the medical device could be fixated to the pelvic bone without penetration of the cortex of the pelvic bone. It is also conceivable that the medical device is adapted to be fixated to the pelvic bone by means of said elastic member exerting a clamping force on the pelvic bone.

Material

The medical device according to any of the embodiments above could comprise at least one of the materials: polyethylene based material, PTFE, Corian, titanium, stainless steel, wolfram, other metal material, a combination of metal material, carbon fiber, boron, a combination of metal and plastic materials, a combination of metal and carbon based material, a combination of carbon and plastic based material, multi-material, wherein one material comprise a flexible material, multi-material, wherein one material comprise an elastic material, multi-material, wherein one material comprising more parts than the other at least one material, PE, and an acrylic polymer. It is also conceivable that the medical device comprises a self lubricating material. In cases where the medical device does not comprise a self lubricating material or if the self lubricating material is not sufficient it is conceivable that the medical device is adapted to be lubricated after insertion in the hip joint.

According to one embodiment the medical device could be adapted to be lubricated after insertion in the hip joint. It is furthermore conceivable that the medical device comprises a self lubricating material such as PTFE.

The Acetabulum Surface

The present invention further relates to a medical device for treating hip joint osteoarthritis in a human patient by providing at least one artificial hip joint surface. The hip joint has a ball shaped caput femur as the proximal part of the femoral bone with a convex hip joint surface and a bowl shaped acetabulum as part of the pelvic bone with a concave hip joint surface.

The medical device comprises an artificial concave hip joint surface, adapted to be fixated to at least one of: caput femur, collum femur or another part of the femoral bone According to one embodiment, the medical device comprises an artificial concave hip joint surface adapted to be inserted through a hole in the pelvic bone of the human patient.

According to one embodiment, the medical device comprises an artificial concave hip joint surface adapted to be inserted through a hole in the hip joint capsule of the human patient.

According to one embodiment, the medical device comprises an artificial concave hip joint surface adapted to be inserted through a hole in the femoral bone of the human patient.

According to one embodiment the artificial concave hip joint surface is further adapted to be placed in connection with an artificial replacement of the convex hip joint surface. The artificial replacement could be adapted to be fixated to the pelvic bone.

According to one embodiment the artificial concave hip joint surface comprises at least two artificial hip joint surface parts adapted to be placed in connection with each other after the insertion in the human patient.

The at least two artificial hip joint surface parts could be adapted to be inserted through a hole in the pelvic bone from the opposite side from acetabulum of the human patient, said hole having a diameter less than the largest diameter of said medical device. It is also conceivable that the at least two artificial hip joint surface parts are adapted to be inserted through a hole in the femoral bone or the hip joint capsule of the human patient. The hole having a diameter less than the largest diameter of said medical device.

According to any of the embodiments above, at least one of said at least Iwo artificial hip joint surface parts could be adapted to serve as base part to which at least one additional artificial caput femur surface part can be connected.

The connection of said at least two artificial hip joint surface parts could be performed using at least one of: at least one screw, at least one pin, at least one portion of at least one of the parts adapted to be introduced into the other part, the parts being adapted to be sliding into the other part, form fitting, welding, adhesive, pin, wire, a ball mounted into a bowl being portions of said parts, a male portion of one part mounted into a female portion of the other part, a key introduced into a lock being portions of said parts, band, or other mechanical connecting members. It is also conceivable that the at least two artificial hip joint surface parts are adapted to mechanically connect to each other using self locking members, in which case the self locking members could be assisted by adhesive or bone cement.

According to one embodiment of the present invention the medical device comprises at least one elastic member. The at least one elastic member could be adapted for changing the largest diameter or largest cross-sectional distance of the medical device for insertion through a hole having a diameter smaller than said largest diameter or cross-sectional distance of said medical device.

Fixation

To fixate the medical device according to the present invention it is conceivable that the medical device comprises a fixation support to anchor said artificial concave hip joint surface. The fixation support is adapted to anchor said artificial concave hip joint surface to the caput femur, the collum femur or another part of the femoral bone of the human patient, to at least partly support the load applied to the hip joint in normal use.

According to one embodiment the fixation support comprises a displaceable part or section, and wherein said displaceable part or section is adapted to carry the load applied to the hip joint in normal use.

According to one embodiment the medical device could be adapted to be fixated to caput femur, the collum femur or the femoral bone using at least one of: at least one screw, at least one pin, at least one portion of at least one of the parts adapted to be introduced into the other part, the parts being adapted to be sliding into the other part, form fitting, welding, adhesive, pin, wire, a ball mounted into a bowl being portions of said parts, a male portion of one part mounted into a female portion of the other part, a key introduced into a lock being portions of said parts, band, or other mechanical connecting members. It is also conceivable that the fixation is done using self locking members, in which case the self locking members could be assisted by adhesive or bone cement.

According to one embodiment the medical device could be fixated to the caput femur, the collum femur or the femoral bone without penetration of the cortex of the pelvic bone. It is also conceivable that the medical device is adapted to be fixated to the caput femur, the collum femur or the femoral bone by means of said elastic member exerting a clamping force on the caput femur, collum femur or femoral bone.

Material

The medical device according to any of the embodiments could comprise at least one of the materials: polyethylene based material, PTFE, Corian, titanium, stainless steel, wolfram, other metal material, a combination of metal material, carbon fiber, boron, a combination of metal and plastic materials, a combination of metal and carbon based material, a combination of carbon and plastic based material, multi-material, wherein one material comprise a flexible material, multi-material, wherein one material comprise an elastic material, multi-material, wherein one material comprising more parts than the other at least one material, PE, and an acrylic polymer. It is also conceivable that the medical device comprises a self lubricating material. In cases where the medical device do not comprise a self lubricating material or if the self lubricating material is not sufficient it is conceivable that the medical device is adapted to be lubricated after insertion in the hip joint.

The System

The present invention further relates to a medical device system for treating hip joint osteoarthritis in a human patient by providing at least two hip joint surfaces. The system comprising the artificial convex hip joint surface according to any of the embodiments above and the artificial concave hip joint surface according to any of the embodiments above.

The artificial convex hip joint surface in the medical device system could be adapted to be placed, at least partly, inside of said artificial concave hip joint surface.

According to one embodiment the artificial convex hip joint surface comprises a largest diameter and said artificial concave hip joint surface could be adapted to travel beyond the largest diameter of the artificial convex hip joint surface.

According to one embodiment the medical device system has a ball shaped caput femur as the proximal part of the femoral bone with a convex hip joint surface, and a bowl shaped acetabulum as part of the pelvic bone with a concave hip joint surface. The artificial convex hip joint surface could be adapted to be placed, at least partly, inside of the caput femur.

According to one embodiment the medical device could be adapted to be lubricated after insertion in the hip joint. Said lubrication is preferably done with a biocompatible lubricator such as hyaluronic acid. It is furthermore conceivable that the medical device comprises a self lubricating material such as PTFE.

Centering Device

According to one embodiment the medical device comprising an artificial acetabulum or an artificial acetabulum surface, wherein said elongated member is adapted to centre and hold said artificial acetabulum or an artificial acetabulum surface during fixation in the hip joint.

According to one embodiment the medical device comprising an artificial caput femur or an artificial caput femur surface, wherein said elongated member is adapted to centre and hold said artificial caput femur or an artificial caput femur during fixation in the hip joint.

According to one embodiment said elongated member is adapted to centre and hold both said artificial caput femur or an artificial caput femur and said artificial acetabulum or an artificial acetabulum surface during fixation in the hip joint.

According to one further embodiment of the medical device, the artificial caput femur surface comprises a convex form towards the centre of the hip joint and the artificial acetabulum surface comprises a concave form towards the centre of the hip joint. The artificial caput femur surface and the artificial acetabulum surface is constructed to be placed in the hip joint in a opposite position towards each other, thus; the artificial convex caput femur surface is adapted to be fixated to the pelvic bone of the human patient, and the artificial concave acetabulum surface is adapted to be fixated to the femoral bone of the human patient.

According to one embodiment the artificial acetabulum or artificial acetabulum surface is adapted to be centered and held by said elongated member, during fixation in the hip joint.

According to one embodiment the artificial caput femur or an artificial caput femur surface is adapted to be centered and held by the elongated member, during fixation in the hip joint.

The Method

A further aspect of the present invention is a method of treating hip joint osteoarthritis in a human patient by providing at least one hip joint surface. The method comprises the steps of: fixating the artificial convex hip joint surface, according to any of the embodiments above, to the pelvic bone, and fixating the artificial concave hip joint surface according to any of the embodiments above to at least one of; the caput femur, the collum femur or the femoral bone of the human patient.

The method could further comprise, the steps of: cutting the skin of the human patient, dissecting an area of the pelvic bone on the opposite side from the acetabulum, creating a hole in said dissected area, said hole passing through the pelvic bone and into the hip joint of the human patient, inserting said artificial hip joint surfaces into the hip joint through said hole. After the steps of fixating the artificial convex hip joint surface, according to any of the embodiments above, to the pelvic bone, and fixating the artificial concave hip joint surface according to any of the embodiments above to at least one of; the caput femur, the collum femur or the femoral bone of the human patient, the method further comprises the steps of: Closing the hole in the pelvic bone using bone material or a prosthetic part and closing, preferable in layers, the hip area of the human patient using sutures or staples.

According to a second embodiment the method is a method of treating hip joint osteoarthritis by providing artificial hip joint surfaces according to any of the embodiments above. The hip joint comprises a ball shaped caput femur as the proximal part of the femoral bone with a convex hip joint surface and a bowl shaped acetabulum as part of the pelvic bone with a concave hip joint surface, the method comprises the steps of: cutting the skin of the human patient, dissecting an area of the hip joint, creating a hole in the hip joint capsule, inserting said artificial hip joint surfaces into the hip joint through said hole in the hip joint capsule, fixating the artificial convex hip joint surface device to the pelvic bone, fixating the concave artificial hip joint surface to at least one of; the caput femur, the collum femur or the femoral bone, and closing, preferable in layers, the hip area of the human patient using sutures or staples or adhesive.

According to a third embodiment the method of treating hip joint osteoarthritis by providing artificial hip joint surfaces according to any of the embodiments above is a arthroscopic method. The hip joint comprises a ball shaped caput femur as the proximal part of the femoral bone with a convex hip joint surface and a bowl shaped acetabulum as part of the pelvic bone with a concave hip joint surface, the method comprises the steps of: inserting a needle or a tube like instrument into the patient's body, using the needle or tube like instrument to fill a part of the patient's body with gas and thereby expanding a cavity within said body, placing at least two arthroscopic trocars in said cavity, inserting a camera through one of the arthroscopic trocars into said cavity, inserting at least one dissecting tool through one of said at least two arthroscopic trocars, dissecting an area of the pelvic bone on the opposite side from the acetabulum, creating a hole in said dissected area, said hole passing through the pelvic bone and into the hip joint of the human patient, and providing said artificial hip joint surfaces to the hip joint, through said hole in the pelvic bone of the human patient.

According to a third embodiment the method of treating hip joint osteoarthritis by providing artificial hip joint surfaces according to any of the embodiments above is a second arthroscopic method. The hip joint comprises a ball shaped caput femur as the proximal part of the femoral bone with a convex hip joint surface and a bowl shaped acetabulum as part of the pelvic bone with a concave hip joint surface, the method comprises the steps of: inserting a needle or a tube like instrument into the patient's body, using the needle or tube like instrument to fill a part of the patient's body with gas and thereby expanding a cavity within said body, placing at least two arthroscopic trocars in said cavity, inserting a camera through one of the arthroscopic trocars into said cavity, inserting at least one dissecting tool through one of said at least two arthroscopic trocars, dissecting an area of the hip joint, creating a hole in the hip joint capsule, inserting said artificial hip joint surfaces into the hip joint through said hole in the hip joint capsule, fixating the artificial convex hip joint surface device to the pelvic bone, fixating the concave artificial hip joint surface to at least one of; the caput femur, the collum femur or the femoral bone, and closing, preferable in layers, the hip area of the human patient using sutures or staples or adhesive.

According to one embodiment the method of manipulation comprises the steps of; fixating an artificial acetabulum surface to the pelvic bone, wherein said elongated member; centers the artificial acetabulum surface, when the artificial acetabulum surface is fixated in the hip joint.

According to one embodiment the method of manipulation comprises the step of; fixating an artificial caput femur surface to the femoral bone, wherein said elongated member; centers said artificial caput femur surface, when said artificial caput femur surface is fixated in the hip joint.

According to one embodiment, a method of centering an artificial hip joint surface in a hip joint of a human patient is provided. The hip joint comprising a collum femur, being the proximal part of the femoral bone, a caput femur, being the upper extremity of the femoral bone, and an acetabulum, being a bowl shaped part of the pelvic bone, the method comprising the steps of: penetrating the skin of a lateral section of the thigh, creating a hole in the collum femur, along a length axis thereof, reaching an area of the hip joint, placing an elongated member in said hole, wherein said elongated member reaches centrally in said area of the hip joint, and centering said artificial hip joint surface onto said elongated member, wherein the artificial hip joint surface comprises a centre hole for guiding the elongated member, and placing the said artificial hip joint surface in a functional position in the hip joint.

The artificial hip joint surface, according to any of the embodiments above may comprise an artificial convex caput femur or an artificial convex caput femur surface or an artificial concave acetabulum or an artificial concave acetabulum surface.

According to one embodiment the step of fixating said artificial acetabulum surface further comprises the step of placing a locking member in connection with the artificial acetabulum surface, such that said artificial acetabulum surface remains clasped to said surgically cut femoral bone.

According to one embodiment the step of placing a locking member comprises the step of placing a locking member encircling the artificial acetabulum surface and the surgically cut caput femur.

The collum femur has a longitudinal extension, and a fixating member at least partly be positioned on and stabilized by the cortical bone of said stabilizing part of the collum femur from two different aspects of the collum femur, the method could comprise the steps of; positioning and stabilizing said fixating member from the inside of said stabilizing part of the collum femur, substantially perpendicular to the longitudinal extension thereof, and from the acetabulum side substantially in line with the longitudinal extension of the collum femur.

The collum femur has a longitudinal extension and a fixating member at least partly be positioned on, and stabilized by the cortical bone of said stabilizing part of the collum femur from three different aspects of the collum femur. The method could comprise the steps of; positioning and stabilizing said fixating member from the inside of said stabilizing part of the collum femur substantially perpendicular to the longitudinal extension thereof, from the acetabulum side substantially in line with the longitudinal extension of the collum femur and from the outside of the collum femur substantially perpendicular to the longitudinal extension thereof.

Please note that any embodiment or part of embodiment as well as any method or part of method could be combined in any way. All examples herein should be seen as part of the general description and therefore possible to combine in any way in general terms.

BRIEF DESCRIPTION OF DRAWINGS

The invention is now described, by way of example, with reference to the accompanying drawings, in which:

FIG. 4a shows the reaming of the collum and caput femur,

FIG. 4b shows the injecting of an adhesive in the acetabulum

FIG. 5 shows the collum and caput femur when a medical device gas been fixated,

FIG. 31 shows the hip joint in section when the method of supplying the medical device is conducted according to another embodiment, FIG. 32 shows the step of applying an adhesive to the concave surface created by the reamer, FIG. 33 shows the step of providing a medical device comprising an artificial concave hip joint surface.

DETAILED DESCRIPTION

Figure 1A:
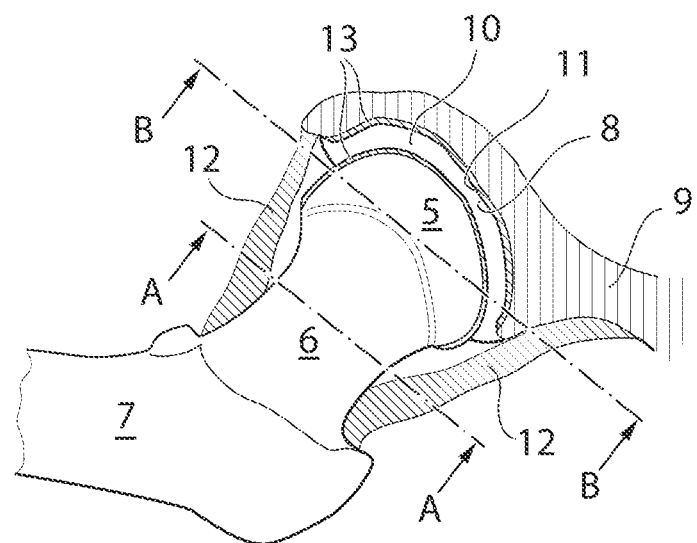
FIG. 1a shows the hip joint in section.

In the following a detailed description of preferred embodiments of the present invention will be given. In the drawing figures, like reference numerals designate identical or corresponding elements throughout the several figures. It will be appreciated that these figures are for illustration only and are not in any way restricting the scope of the invention. Thus, any references to direction, such as "up" or "down", are only referring to the directions shown in the figures. Also, any dimensions etc. shown in the figures are for illustration purposes.

Functional hip movements are to be understood as movements of the hip that at least partly correspond to the natural movements of the hip. On some occasions the natural movements of the hip joint might be somewhat limited or altered after hip joint surgery, which makes the functional hip movements of a hip joint with artificial surfaces somewhat different than the functional hip movements of a natural hip joint.

The functional position of an implantable medical device or prosthesis is the position in which the hip joint can perform functional hip movements. The final position is to be understood as a functional position in which the medical device needs no further position change.

Arthroscopy is to be understood as key hole surgery performed in a joint, since the arthroscopic procedure could be performed in the abdomen of the patient some of the steps of this arthroscopic procedure is more laparoscopic, however for the purpose of this invention the two terms arthroscopy and laparoscopy is used synonymously and for the purpose of this invention the main purpose of these methods are is that they are minimally invasive.

The medical device according to any of the embodiments could comprise at least one material selected from a group consisting of: polytetrafluoroethylene (PTFE), perfluoroalkoxy (PFA) and fluorinated ethylene propylene (FEP). It is furthermore conceivable that the material comprises a metal alloy, such as cobalt-chromium-molybdenum molybdenum or titanium or stainless steel, or polyethylene, such as cross-linked polyethylene or gas sterilized polyethylene. The use of ceramic material is also conceivable, in the contacting surfaces or the entire medical device such as zirconium or zirconium dioxide ceramics or alumina ceramics. The part of the medical device in contact with human bone for fixation of the medical device to human bone could comprise a poorhouse structure which could be a porous micro or nano-structure adapted to promote the growth-in of human bone in the medical device for fixating the medical device. The porous structure could be achieved by applying a hydroxy-apatite (HA) coating, or a rough open-pored titanium coating, which could be produced by air plasma spraying, a combination comprising a rough open-pored titanium coating and a HA top layer is also conceivable. The contacting parts could be made of a self lubricated material such as a waxy polymer, such as PTFE, PFA, FEP, PE and UHMWPE, or a powder metallurgy material which could be infused with a lubricant, which preferably is a biocompatible lubricant such as a Hyaluronic acid derivate. It is also conceivable that the material of contacting parts or surfaces of the medical device herein is adapted to be constantly or intermittently lubricated. According to some embodiments the parts or portions of the medical device could comprise a combination of metal materials and/or carbon fibers and/or boron, a combination of metal and plastic materials, a combination of metal and carbon based material, a combination of carbon and plastic based material, a combination of flexible and stiff materials, a combination of elastic and less elastic materials, Corian or acrylic polymers.

FIG. 1a shows the hip joint of a human patient in section. The hip joint comprises a caput femur 5 placed at the very top of collum femur 6 which is the top part of the femoral bone 7. The caput femur is in connection with the acetabulum 8, which is a bowl shaped part of the pelvic bone 9. Both the caput femur surface 10 and the acetabulum surface 11 is covered with articular cartilage 13 which acts as a cushion in the hip joint. In patients with hip joint osteoarthritis, this articular cartilage 13 is abnormally worn down due to a low grade inflammation. The hip joint is surrounded by the hip joint capsule 12 which provides support for the joint and hinders luxation. After conventional hip joint surgery, penetrating the hip joint capsule 12, the capsule 12 is dramatically weakened due to the limited healing possibilities of its ligament tissue. By performing hip joint surgery without damaging the hip joint capsule 12 the patient can fully recover and place equal amount of strain on an artificial joint as is possible on a natural one.

Figure 1B:
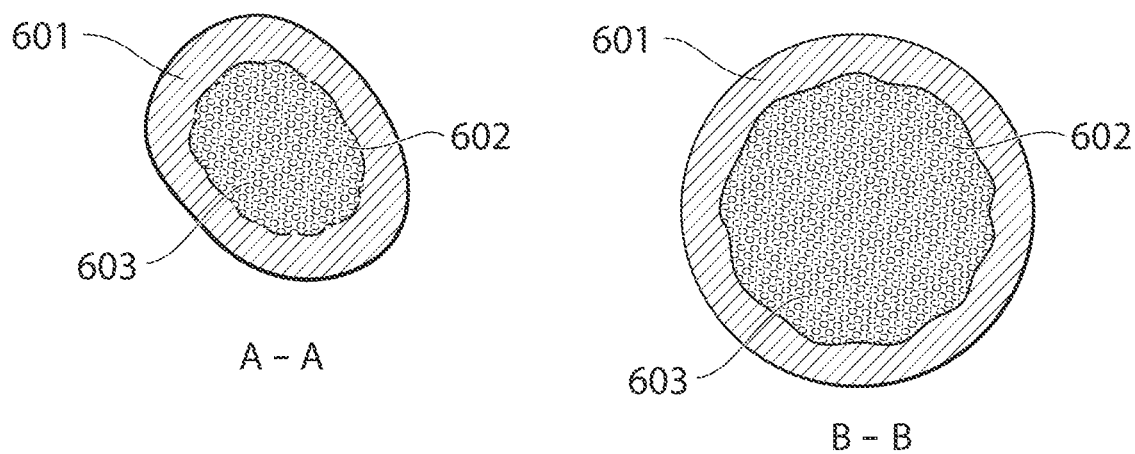
FIG. 1b shows the collum femur in section.

FIG. 1b shows a section A-A of the collum femur, as shown in FIG. 1. The section A-A shows the collum femur comprising cortical bone 601, the outer more sclerotic bone, and cancellous bone 602, the inner porous bone located in the bone marrow 603. Further, FIG. 1b shows a section B-B of the caput femur, perpendicular to the length axis of the collum 6 and caput 5 femur.

Figure 2:
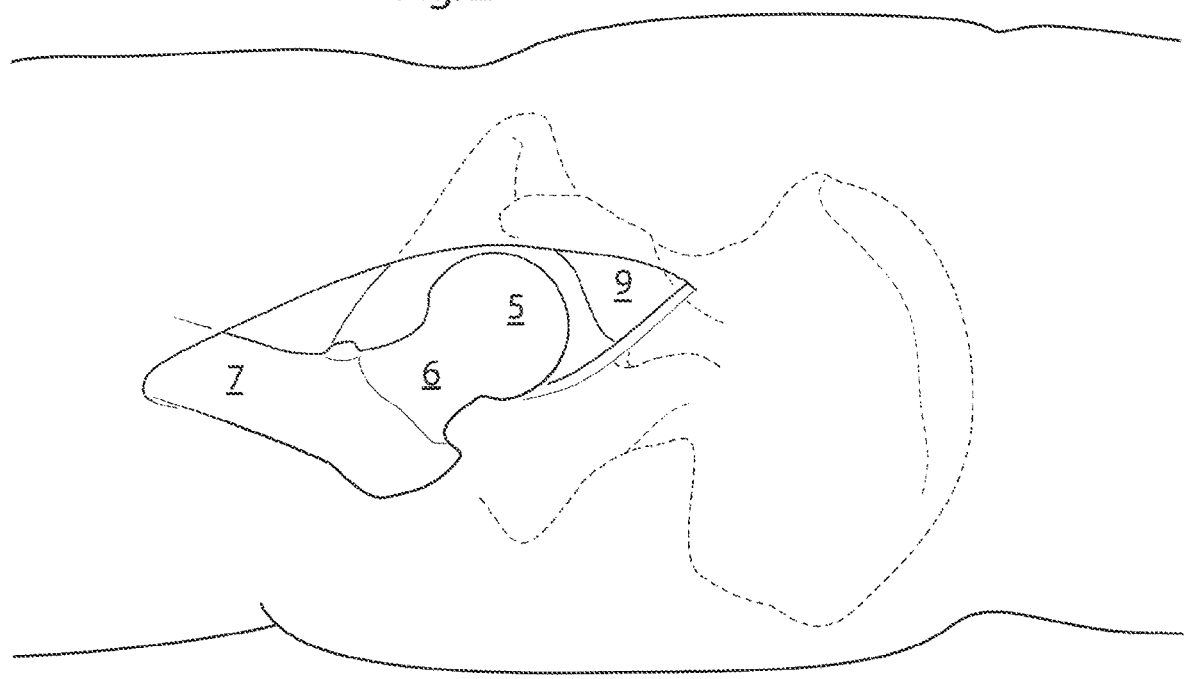
FIG. 2 shows the exposing of the caput femur through an incision in the thigh.

FIG. 2 shows a lateral view of a human patient when an incision in the thigh region has been made. The femoral bone 7 comprising the collum femur 6 and the caput femur 5 has been dislocated from its usual position in the hip joint, in connection with the acetabulum, which is a part of the pelvic bone 9, the caput femur 5 being a part of the hip joint normally being covered by the hip joint capsule.

Figure 3:
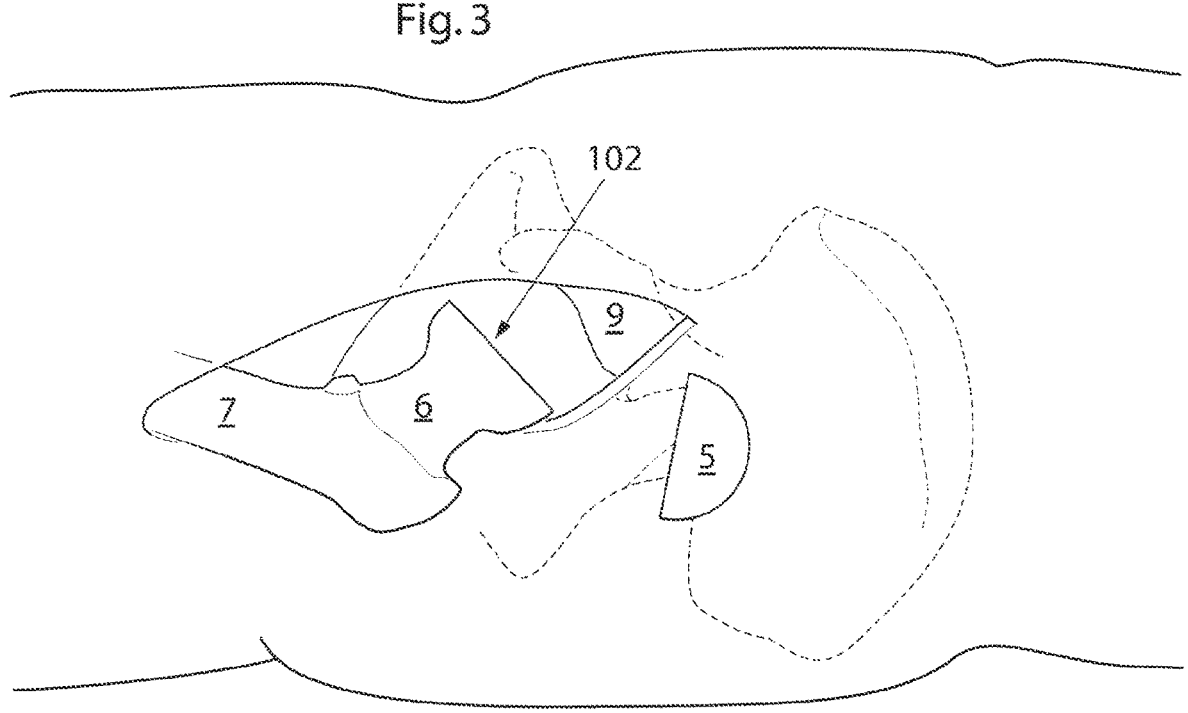
FIG. 3 shows the step of removing a proximal part of the caput femur.

FIG. 3 shows the proximal part of the caput femur 5 being removed e.g. by means of a bone saw. A surface of a section 102 is thus created perpendicularly to a length axis of the collum femur 6

FIG. 4a shows the reaming of the collum femur 6 and caput femur 5 using a reamer 40 connecting to an elongated member 21 by a connecting section 101. The reamer 40 creating a hemi-spherical cavity, having a concave surface 103, centrally placed in the caput 5 and collum femur 6.

FIG. 4b shows the step of applying an adhesive 106 to the created hemi-spherical cavity in the femoral bone using an injecting member 104 having an injecting nozzle 105. In the embodiment shown in FIG. 4b the injecting member is inserted into an area of the hip joint through a hole 18 in the pelvic bone 9, however it is equally conceivable that the injecting member is inserted through the hip joint capsule 12 or the femoral bone 7.

FIG. 5 shows the femoral bone 7 when a medical device 109 having a concave contacting surface has been provided to the hemi-spherical cavity, centrally placed in the caput 5 and collum femur. An elastic layer 109b adapted to absorb shocks from the femoral bone has been placed between the surface 109c adapted to be in contact with the artificial caput femur surface, and the femoral bone 7, 6. The elastic layer 109b could be an elastic polymer layer, such as a polyurethane or silicone layer. Having a layer absorbing shocks in the hip joint reduces the risk of fastening elements in contact with bone being affected by strains such that the fastening elements are loosened from their respective fastening positions, it also increases the comfort for the patient.

Figure 6A:
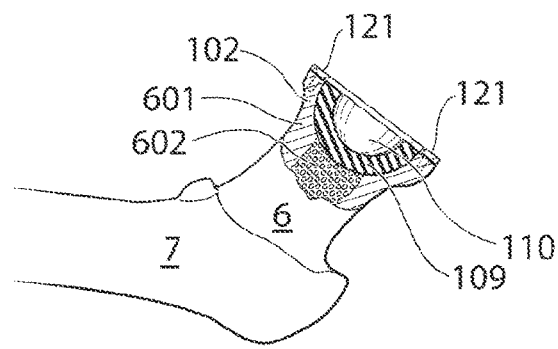
FIG. 6a shows the femoral bone when a medical device having a concave contacting surface has been provided to the hemi-spherical cavity shows the reaming of the acetabulum.

FIG. 6a shows the femoral bone 7 when a medical device having a concave contacting surface 110 has been provided to the hemi-spherical cavity, centrally placed in the caput 5 and collum femur. The medical device has been fixated to the femoral bone 7 using screws 121 placed aligned with the caput and collum femur center axis and entering the cortical bone of the caput femur.

Figure 6B:
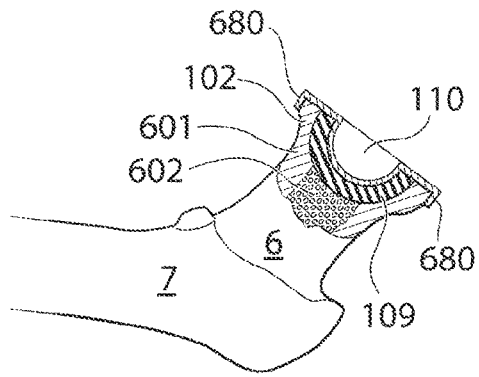
FIG. 6b shows the femoral bone when a medical device having a concave contacting surface has been provided to the hemi-spherical cavity.

FIG. 6b shows the femoral bone 7 when a medical device having a concave contacting surface 110 has been provided to the hemi-spherical cavity, centrally placed in the caput 5 and collum femur. The medical device comprises fixating portions 680 extending on the outside of the surface of a section 102 of the surgically cut caput femur, comprising cortical bone in the periphery thereof, thereby stabilizing the medical device with the artificial concave acetabulum surface 110 in the surgically cut caput femur.

Figure 6C:
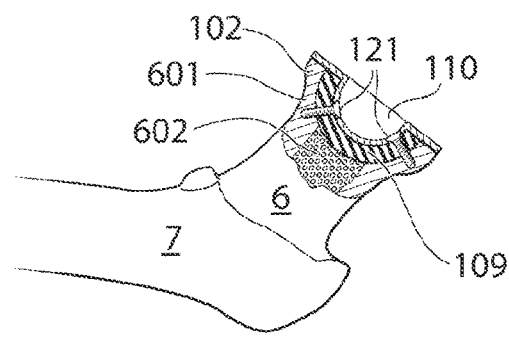
FIG. 6c shows an alternative embodiment, in which the medical device has been fixated to the surgically cut caput femur using screws.

FIG. 6c shows an alternative embodiment, in which the medical device has been fixated to the surgically cut caput femur using screws 121 entering the cortical bone 601 of the caput femur.

Figure 6D:
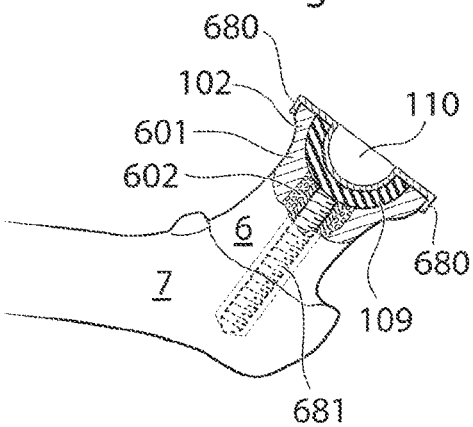
FIG. 6d shows yet another embodiment, in which the medical device is fixated to the femoral bone using fixating portions.

FIG. 6d shows yet another embodiment, in which the medical device is fixated to the femoral bone using fixating portions, in accordance with the embodiment described with reference to FIG. 6b, and an elongated member 681. The elongated member is according to this embodiment a threaded member 681 extending along the collum and caput femur center axis, in the cancellous bone 602 of the collum femur, and entering the cortical bone 601 of the femoral bone, on the inside thereof, in the area of the greater trochanter. The threaded elongated member 681 creates an axial force when pulled pressing the medical device towards the surface of a section 102 of the surgically cut caput femur, thereby stabilizing and fixating the medical device in the concave cavity created in the caput femur.

Figure 6E:
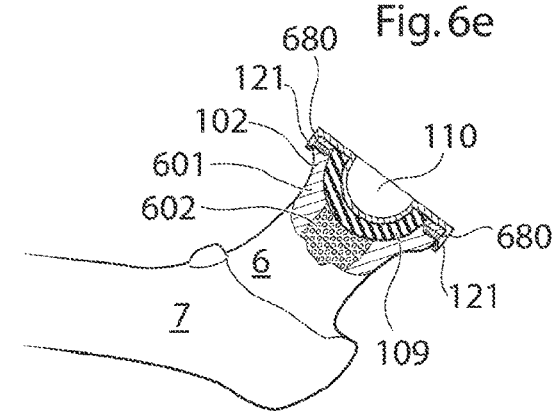
FIG. 6e shows yet an alternative embodiment of the medical device in which the fixating portions are additionally fixated using screws.

FIG. 6e shows yet an alternative embodiment of the medical device in which the fixating portions 680 are additionally fixated using screws 121 placed from the outside of the surgically cut caput femur, perpendicularly to the collum and caput femur center axis.

Figure 7A:
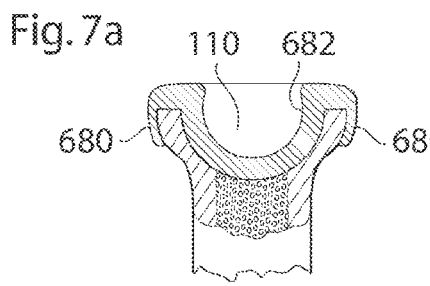
FIG. 7a shows the medical device in an embodiment in which the fixating portions extends beyond the greatest circumference of the surgically cut caput femur.

FIG. 7a shows the medical device in an embodiment in which the fixating portions 680 extends beyond the greatest circumference of the surgically cut caput femur and thereby clasps the medical device to the surgically cut caput femur, fixating the medical device thereon. The concave contacting surface 110 is also adapted to travel beyond the equator of an artificial caput femur which is placed in the artificial acetabulum when mounted into a functioning artificial hip joint, and clasping the artificial caput femur when mounted therein.

Figure 7B:
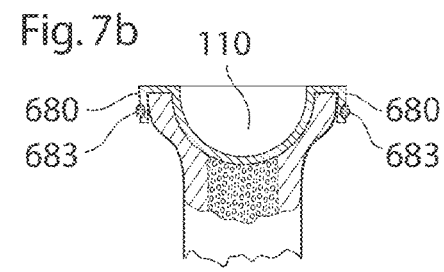
FIG. 7b shows yet another embodiment where the medical device is additionally fixated using a fixating band.

FIG. 7b shows yet another embodiment where the medical device is additionally fixated using a fixating band 683 encircling the fixating portions of the medical device and thereby further clasping the medical device to the surgically cut caput femur.

Figure 7C:
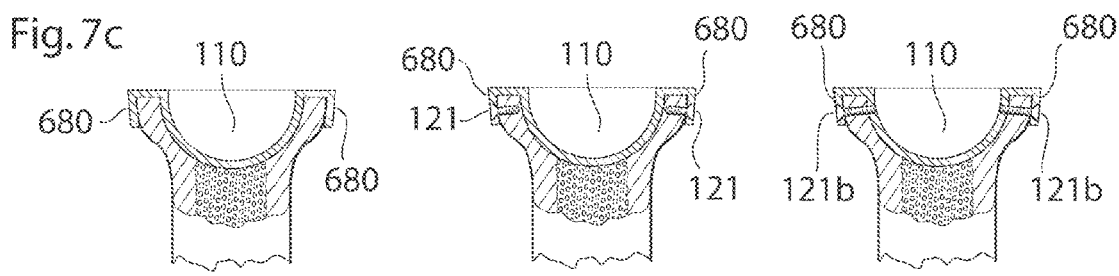
FIG. 7c shows three different embodiment of medical devices comprising fixating portions.

FIG. 7c shows three different embodiment of medical devices comprising fixating portions 680 which are slightly tilted towards the collum and caput femur center axis, thereby clasping a portion of the surgically cut caput femur for fixating the medical device to the surgically cut caput femur. The three different embodiments shown is first, without screws 121, second, with screws entering the cortical bone, and third, with screws penetrating the cortical bone and entering the medical device on the inside of the concave cavity, which enables the screws to squeeze a portion of the cortical bone for tight fixation of the medical device.

Figure 7D:
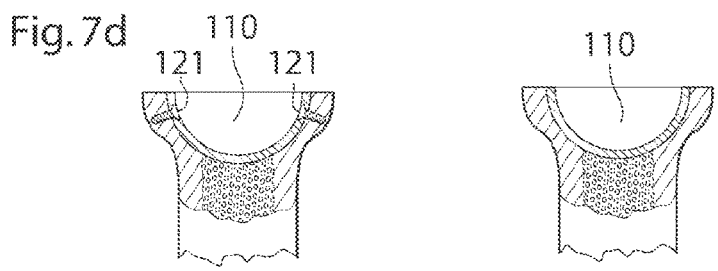
FIG. 7d shows two embodiments in which the concave contacting surface only comprises the part placed inside of the concave cavity.

FIG. 7d shows two embodiments in which the concave contacting surface 110 only comprises the part placed inside of the concave cavity. The first embodiment shows the acetabulum surface 110 fixated to the concave cavity using screws 121, whereas the second embodiment shows the artificial acetabulum surface fixated without screws, such as using an adhesive.

Figure 7E:
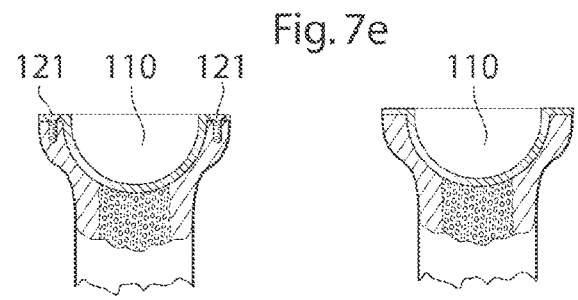
FIG. 7e shows two embodiments in which the artificial acetabulum surface extends into a portion placed on the surface of a section created when the caput femur is surgically cut.

FIG. 7e shows two embodiments in which the artificial acetabulum surface extends into a portion placed on the surface of a section created when the caput femur is surgically cut. In the first embodiment the medical device is fixated using screws entering the cortical bone, whereas in the second embodiment the artificial contacting surface is fixated without screws, such as using an adhesive.

Figure 7F:
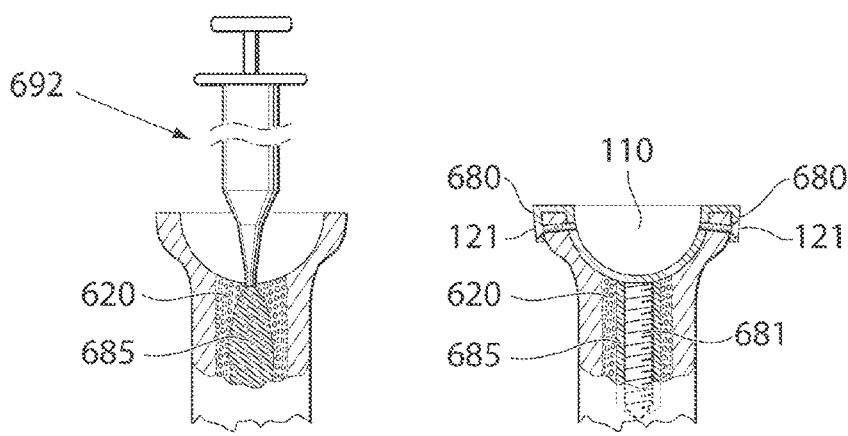
FIG. 7f describes an embodiment in which the medical device is further fixated using an elongated member.

FIG. 7f describes an embodiment in which the medical device is further fixated using an elongated member 681, fixating portions 680, and screws 121 placed between the fixating portions 680 and the inside of the artificial acetabulum contacting surface 110. The elongated member 681 is according to this embodiment a threaded member 681 and the first fig. discloses the preparation of the cancellous bone 602 with a curing fluid 685, such as bone cement, creating a sturdy base for the fixation of the threaded member 681.

Figure 8:
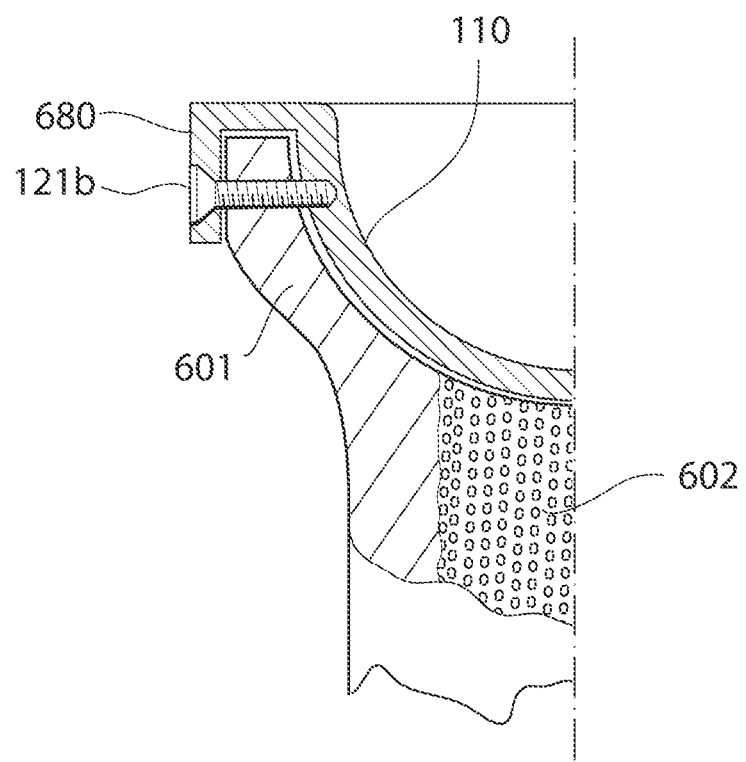
FIG. 8 shows the artificial acetabulum surface in further detail when the artificial acetabulum surface comprises a fixating portion.

FIG. 8 shows the artificial acetabulum surface 110 in further detail when the artificial acetabulum surface comprises a fixating portion 680 extending on the outside of the cortical bone 601. The fixating portion 680 is further fixated using screws 121 placed from the outside, through a hole in the medical device, penetrating the cortical bone 601 of the surgically cut caput femur and entering the medical device placed in the concave cavity in the caput femur.

Figure 9:
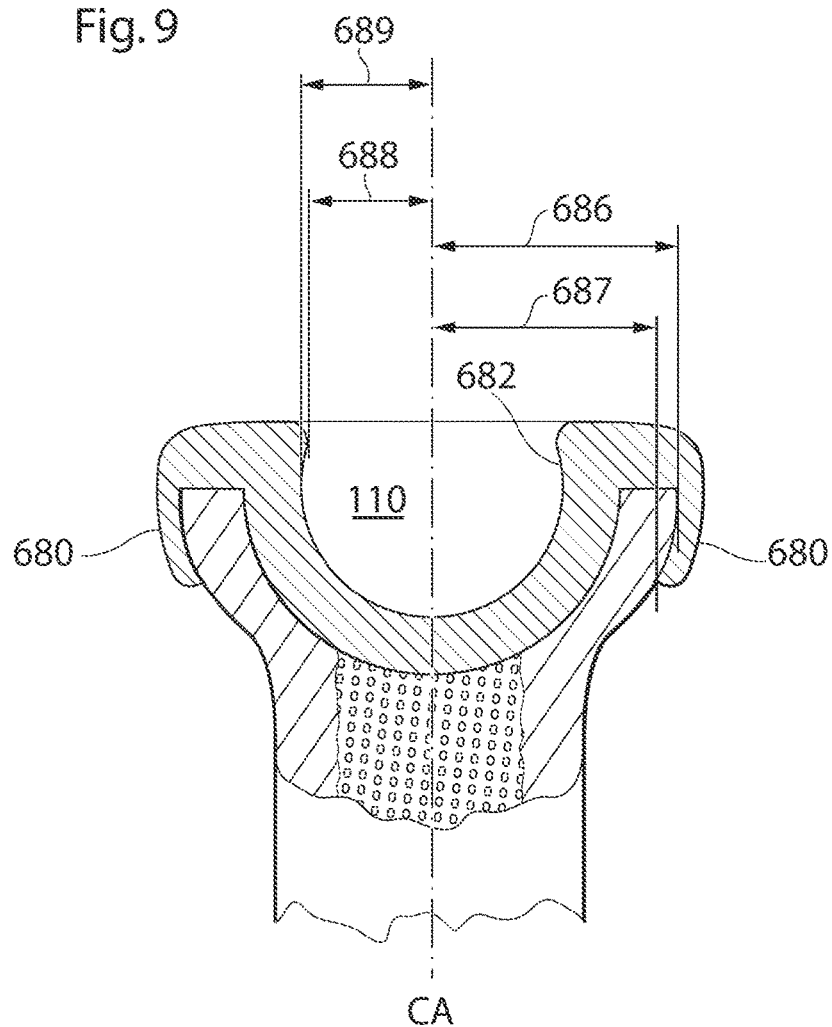
FIG. 9 shows a section of the medical device.

FIG. 9 shows a section of the medical device according to the embodiment also described with reference to FIG. 7a, in further detail. The medical device according to the embodiment in FIG. 9 comprises fixating portions 680 which reaches on the outside of the surgically cut caput femur and clasps the cortical bone of the caput femur. The medical device clasps the caput femur since a distance 687, between the collum and caput femur center axis CA and the fixating portion in shorter than a distance 686 between the collum and caput femur center axis CA and a portion of the fixating portion placed more proximally when the medical device is implanted. On the inside of the artificial concave acetabulum surface, the surface extends beyond the equator of the artificial caput femur adapted to be placed therein. An extending portion 682 clasps the artificial caput femur placed in the artificial acetabulum surface 110 since a distance 688, between the collum and caput femur center axis CA and the inside of the artificial acetabulum surface 110 is shorter than a distance 689 between the collum and caput femur center axis CA and a point on the inside of the artificial acetabulum contacting surface 110 being more distal when the medical device is implanted. In other embodiments, the fixating portions 680 could be operable or adjustable for further fixating the medical device to the cortical bone. The fixating portions 680 could be operable for example by means of a screw for tightening the fixating portions 680 to the cortical bone, which could squeeze the cortical bone between the fixating portions 680 and the part of the medical device placed inside of the femoral bone.

Figure 10A:
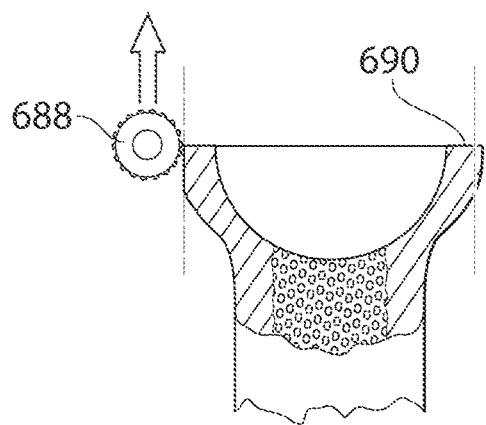
FIG. 10a shows the step of milling the periphery of the cortical bone of the caput femur after the caput femur has been surgically cut.

FIG. 10*a* shows the step of milling the periphery 690 of the cortical bone of the caput femur after the caput femur has been surgically cut, using a milling device 688 adapted therefor. The milling process creates a straighter edge which facilitates the fixation of a medical device on the outside of the caput femur.

Figure 10B:
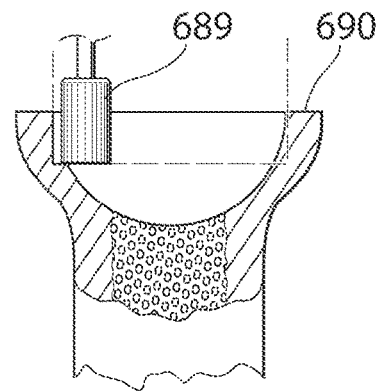
FIG. 10b shows the milling of the inside of the cortical bone of the caput femur after the caput femur has been surgically cut.

FIG. 10*b* shows the milling of the inside of the cortical bone of the caput femur after the caput femur has been surgically cut, using a milling device 689 adapted therefor, creating a straighter edge which facilitates the fixation of a medical device on the inside of the caput femur.

Figure 11:
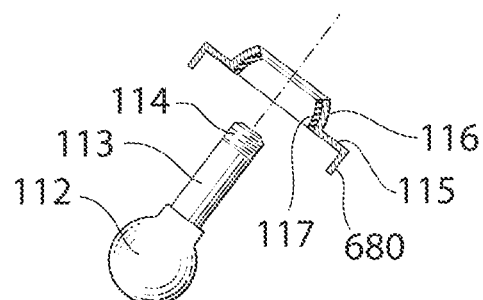
FIG. 11 shows an artificial convex caput femur surface adapted to be placed in an artificial acetabulum surface according to any of the embodiments herein.

FIG. 11 shows an artificial convex caput femur surface 112 adapted to be placed in an artificial acetabulum surface according to any of the embodiments herein. After the artificial convex caput femur surface has been placed in the artificial acetabulum surface it is locked using a locking member 116 comprising a surface 117 adapted to be in contact with the artificial convex hip joint surface 112. The locking member 116 further comprises fixating members 115 which are adapted to assist in the fixation of the locking member 116 to the caput femur 5 or collum femur 6, which in turns fixates the artificial convex hip joint surface 112. The fixating members comprises a fixating portion 680 which travels on the outside of the surgically cut caput femur for radially stabilizing and fixating the locking member to the surgically cut caput femur. The artificial convex hip joint surface 112 is fixated to an attachment rod 113 comprising a thread 114.

Figure 12:
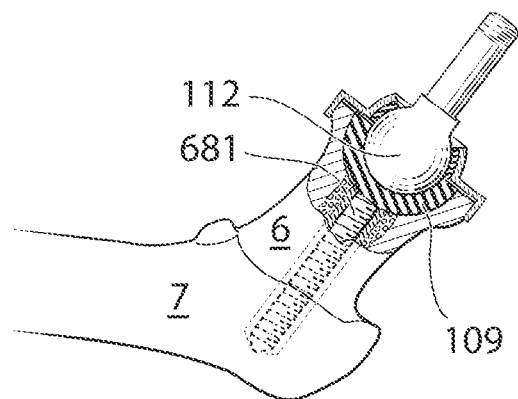
FIG. 12 shows the artificial convex caput femur surface when mounted in an artificial acetabulum surface.

FIG. 12 shows the artificial convex caput femur surface 112 as disclosed with reference to FIG. 11 when mounted in an artificial acetabulum surface 109 placed in a concave cavity in the femoral bone. The artificial acetabulum surface is according to this embodiment is fixated to the femoral bone using an elongated member 681, here being a threaded member placed aligned with the collum and caput center axis.

Figure 13:
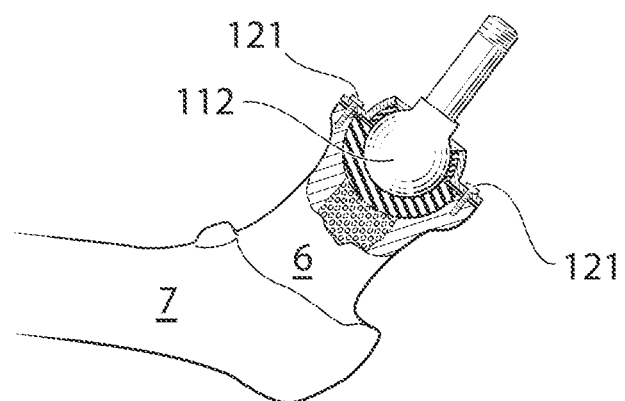
FIG. 13 shows the artificial convex caput femur surface when mounted in an artificial acetabulum surface.

FIG. 13 shows the artificial convex caput femur surface 112 as disclosed with reference to FIG. 11 when mounted in an artificial acetabulum surface 109 placed in a concave cavity in the femoral bone. The artificial acetabulum surface is according to this embodiment is fixated using screws 121 entering the cortical bone of the surgically cut caput femur.

Figure 14:
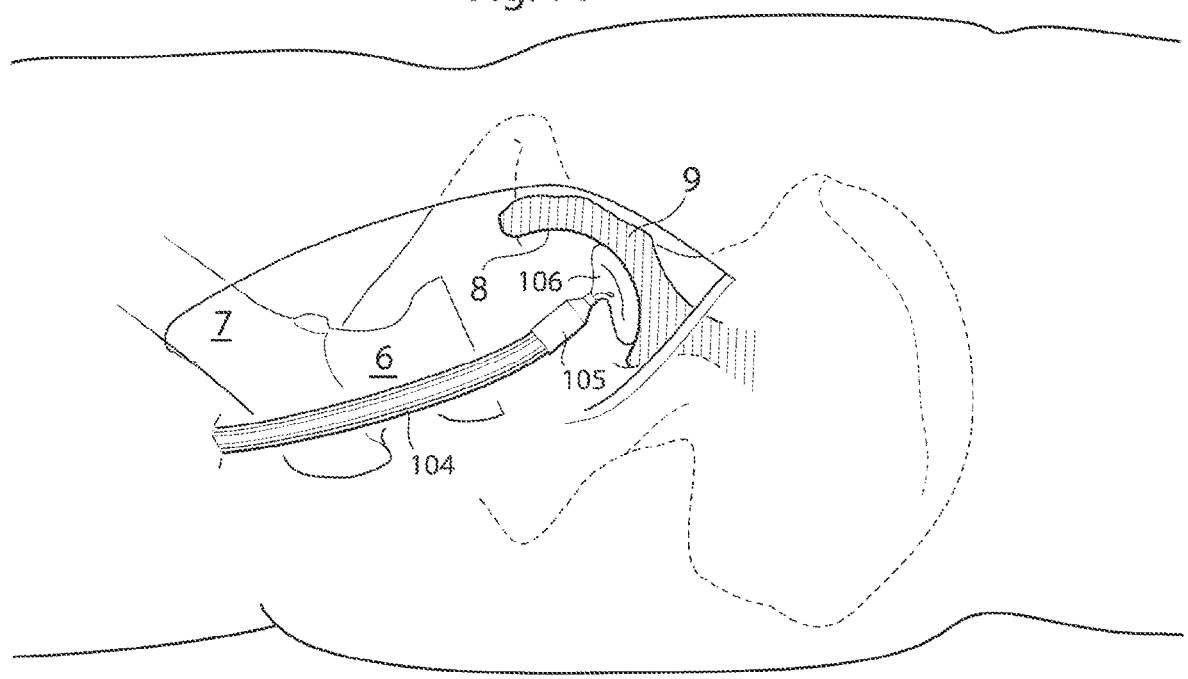
FIG. 14 shows the injection of an adhesive in the acetabulum in the pelvic bone using an injecting member.

FIG. 14 shows the injection of an adhesive 106 in the acetabulum 8 in the pelvic bone 9 using an injecting member comprising an injecting nozzle 105, which is a preparation for the fixation of a medical device to the pelvic bone 9.

Figure 15:
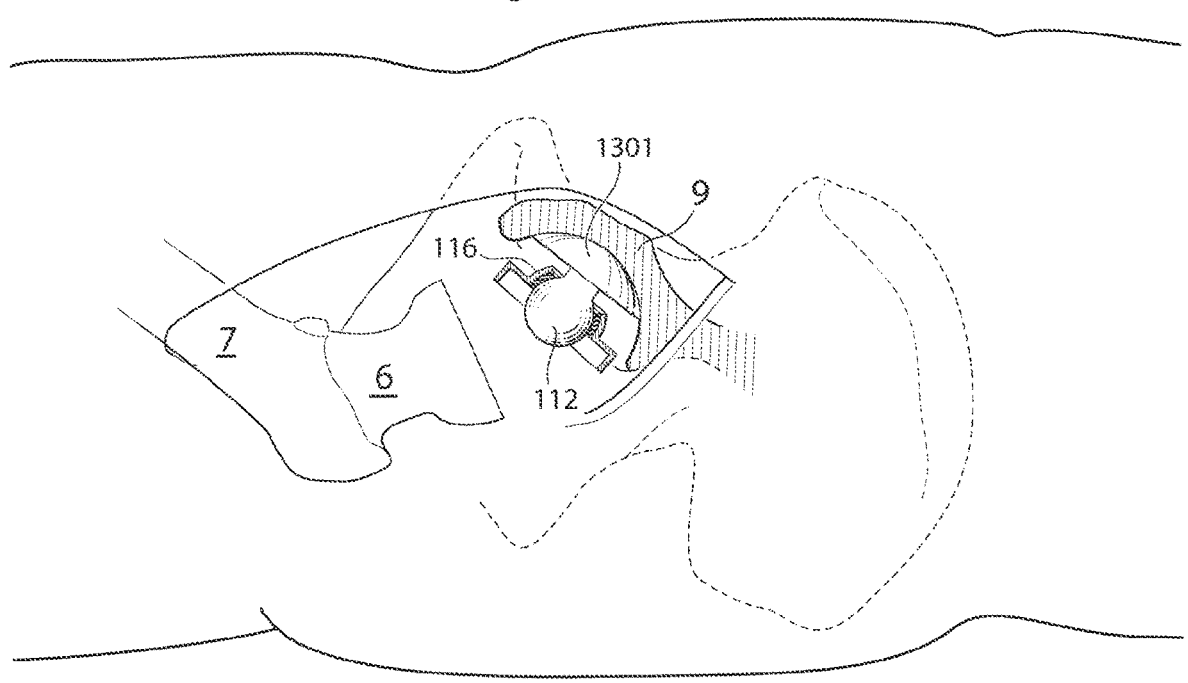
FIG. 15 shows the placing of a medical device in the reamed acetabulum surface of the pelvic bone.

FIG. 15 shows the placing of a medical device in the reamed acetabulum 8 surface of the pelvic bone 9. The medical device comprises a convex hip joint surface 112 fixated to a fixation element 1301, which in turn is fixated to the acetabulum 8 using the injected fluid, which could be assisted or replaced by a mechanical fixation element such as screws. The medical device further comprises a pre-mounted locking member 116 for locking the convex hip joint surface of the concave hip joint surface placed in the caput 5 and collum femur 6 for hindering dislocation of the hip joint when the hip joint is in its functional position.

Figure 16A:
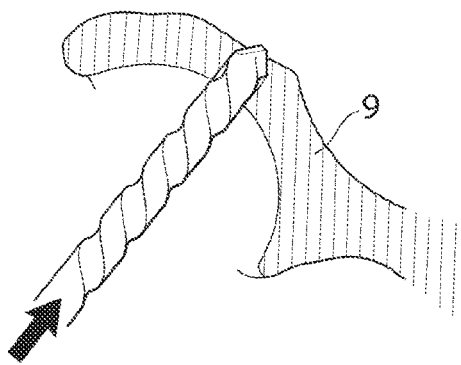
FIG. 16a shows the step of creating a hole in the pelvic bone from the acetabulum side of the pelvic bone.

FIG. 16*a* shows the step of creating a hole in the pelvic bone 9 from the acetabulum side of the pelvic bone 9.

Figure 16B:
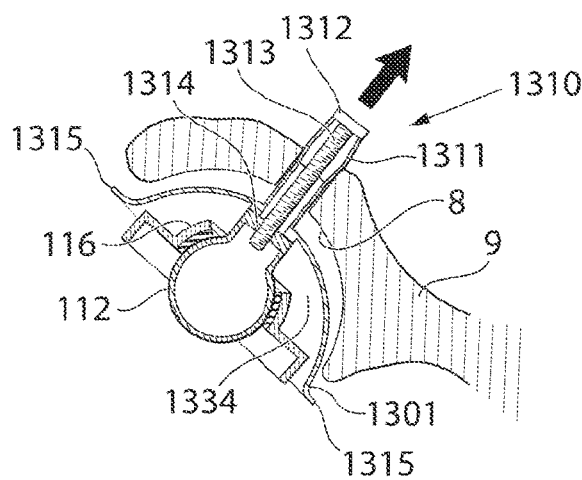
FIG. 16b shows the medical device according to an embodiment in which the medical device comprises a fixation element.

FIG. 16*b* shows the medical device according to an embodiment in which the medical device comprises a fixation element 1301 adapted to fixate the artificial convex caput femur 112 to the pelvic bone 9. The fixation element 1301 comprises a fixation surface 1334 which is adapted to fit into the acetabulum 8. The fixation surface 1334 could be adapted to be fixated against the acetabulum 8 using an adhesive, such as bone cement, applied to the fixation surface 1334 and/or the acetabulum surface 8. The medical device further comprises an elongated element 1310, here being an integrated part of the fixation element 1301. The elongated element 1310 is inserted through the hole in the pelvic bone 9, such that said elongated member 1310 is partially placed on the abdominal side of the pelvic bone 9. After insertion of the elongated member 1310, the elongated member 1310 is structurally changed on the abdominal side of the pelvic bone 9, such that said elongated member 1310 fixates the fixation element 1301 to the pelvic bone 9. According to the embodiment of FIG. 16*b* the elongated member 1310 comprises an expandable portion 1311, and the structural change comprises the expandable portion 1311 changing from a first, non-expanded state, in which the elongated element 1310 is inserted into the hole in the pelvic bone 9 substantially along a length axis of the elongated element 1310 into an expanded state, in which the expandable portion 1311 is expanded in at least one away from the length axis, such that said elongated element 1310 is placed in an expanded state, which fixates the fixation element 1301 to the pelvic bone 9. The expandable portion 1311 according to the embodiment shown in FIG. 16*b* comprises a plurality of expanding elements in connection with an anvil member 1312. A threaded member 1313 is placed centrally in the elongated element 1310 and is in one end connected to an anvil member 1312 and in the other end connected to a threaded portion 1314 of the artificial caput femur 112. By the connection with the threaded member 1313, the anvil member 1312 is adapted to press on the expanding elements following an action performed from the acetabulum side of the pelvic bone 9, such that said expanding elements expand in at least one direction substantially perpendicular to the length axis of the elongated element 1311. The fixation element shown in FIG. 16*b* further comprises a flange 1315 adapted to extend out of the acetabulum 8 and be placed in contact with the pelvic bone 9.

Figure 16C:
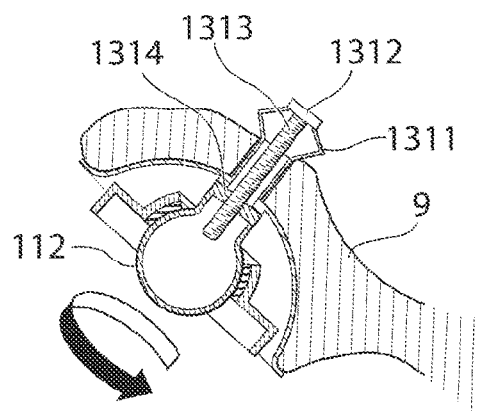
FIG. 16c shows the expandable portion when the anvil member has pressed the expandable elements in two directions.

FIG. 16*c* shows the expandable portion 1311 when the anvil member 1312 has pressed the expandable elements in two directions perpendicular to the length axis of the elongated element 1310 for fixating the elongated element 1310 and the entire artificial caput femur 112 to the pelvic bone 9. The threaded part 1314, being a portion of the artificial caput femur 112, has been partially inserted into the artificial caput femur 112, and thus the anvil member 1312 is pulled towards the hole in the pelvic bone 9.

Figure 16D:
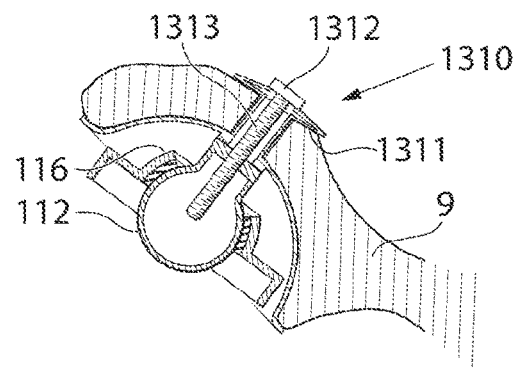
FIG. 16d shows the elongated member in the wholly expanded state fixating the artificial caput femur to the pelvic bone.

FIG. 16*d* shows the elongated member 1311 in the wholly expanded state fixating the artificial caput femur 112 to the pelvic bone 9. In this state the threaded member 1313 is positioned further into the artificial caput femur 112 which is rotated to tighten the expandable elongated element 1310. The locking member 116 is according to this embodiment pre-mounted onto the artificial caput femur 112 when the artificial caput femur 112 is implanted, however, according to other embodiments it is equally conceivable that the locking member 116 is adapted to be mounted after the artificial caput femur 112 has been implanted in the hip joint.

Figure 16E:
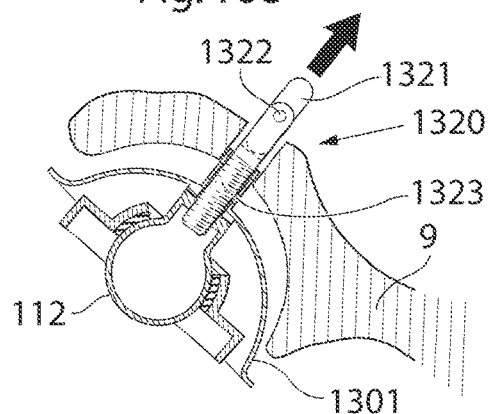
FIG. 16e shows the medical device according to an embodiment in which the implantable medical device comprises an elongated element.

FIG. 16e shows the medical device according to an embodiment in which the implantable medical device comprises an elongated element 1320 comprising a movable locking portion 1321 adapted to have a first and second state, wherein said movable locking portion 1321, in said first state is adapted to be inserted into a hole in the pelvic bone 9, and in said second state is adapted to hinder the elongated element 1320 from passing through said hole in the pelvic bone 9 by said movable locking portion 1321 contacting the surface of the pelvic bone 9 on the abdominal side. FIG. 8f shows the elongated element 1320 in its first state after having passed through the hole in the pelvic bone 9.

Figure 16F:
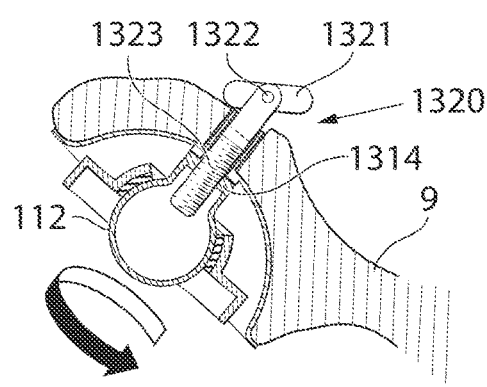
FIG. 16f shows the movable locking portion.

FIG. 16f shows the movable locking portion 1321 changing from the first to the second state at the same time as the artificial caput femur 112, comprising a threaded part 1314, interacts with a corresponding threaded member 1323 being part of the elongated element 1320. The movable locking portion 1321 is pivotally arranged at a pivot point 1322 and changes from the first to the second state using the pivot point 1322.

Figure 16G:
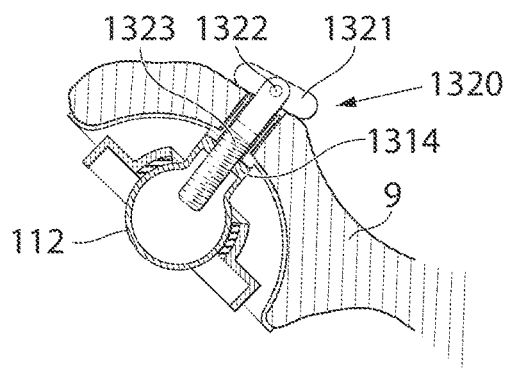
FIG. 16g shows the medical device when the movable member is placed in the second state.

FIG. 16g shows the medical device according to the embodiment of FIGS. 16e and 16f when the movable member 1321 is placed in the second state, in which the artificial caput femur 112 is fixated to the pelvic bone 9 by the movable member 1321 being in contact with the abdominal side of the pelvic bone 9. The artificial caput femur 112 has been tightened using the threaded part 1314 and corresponding threaded member 1323, such that the entire medical device comprising the artificial caput femur 112 is securely fixated to the pelvic bone 9. Similar to the embodiments shown with reference to FIGS. 16b-16d the fixation element 1301 could be further fixated to the acetabulum 8 using an adhesive, such as bone cement, applied to the fixation surface and/or the acetabulum surface 8.

Figure 16H:
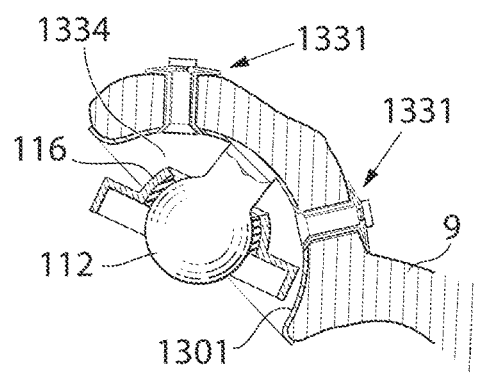
FIG. 16h shows an embodiment in which the fixation element comprises a fixation surface comprising two holes.

FIG. 16h shows an embodiment in which the fixation element comprises a fixation surface 1334 comprising two holes adapted to receive two mechanical fixation elements 1331. In the embodiment of FIG. 8i the mechanical fixation elements 1331 are expanding fixation elements 1331, such as the expanding fixation elements described with reference to FIGS. 16b-16d, however in other embodiments it is equally conceivable that the mechanical fixation elements are elements adapted to fixate the medical device to the internal periphery of the holes, such as screws. Similar to the embodiments shown with reference to FIGS. 16b-16g the fixation element 1301 could be further fixated to the acetabulum using an adhesive, such as bone cement, applied to the fixation surface and/or the acetabulum surface. FIG. 16h shows an embodiment in which the medical device has a pre-mounted locking member 116, however, in other embodiments it is equally conceivable that the locking member 116 is adapted to be mounted after the artificial caput femur 112 has been implanted in the hip joint.

Figure 16I:
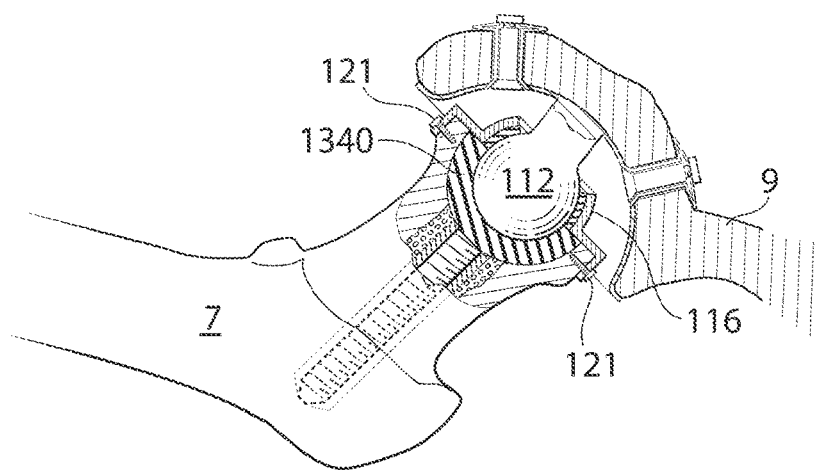
FIG. 16i shows the artificial hip joint in section.

FIG. 16i shows the artificial hip joint in section, when the medical device described with reference to FIG. 16h has been implanted. Furthermore an artificial acetabulum surface 1340 having a concave surface towards the center of the hip joint has been implanted. The artificial acetabulum surface 1340 has been fixated to the femoral bone 7, and placed in movable contact with the artificial caput femur surface 112, thus creating a functioning artificial hip joint. The locking member 116 has been fixated to the femoral bone 7, thus locking the artificial caput femur 112 in the artificial acetabulum surface 1340. The locking member 116 is according to the embodiment shown in FIG. 8j fixated using screws 121, however the screws 121 could be assisted or replaced by an adhesive, such as bone cement.

Figure 17A:
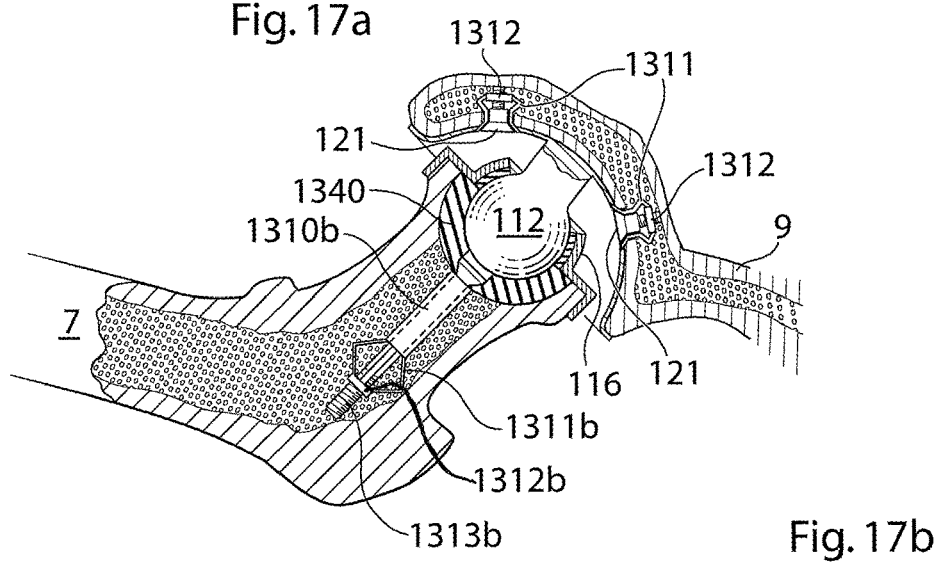
FIG. 17a shows an assembled artificial hip joint with an artificial caput femur surface.

FIG. 17a shows an assembled artificial hip joint with an artificial caput femur surface 112 fixated to the pelvic bone 9 using two fixating members adapted to expand inside of the cortical bone of the pelvic bone 9. The fixating members comprises a screw 121 in connection with an anvil member 1312 affecting an expandable portion 1311 pressing the expandable members in two directions perpendicular to the length axis of the fixation members for fixating the artificial caput femur 112 to the pelvic bone 9. The artificial acetabulum 1340 is fixated to the femoral bone 7 using an elongated member 1310b placed in the cancellous bone and aligned with the caput and collum femur center axis. The elongated member comprises an expandable portion 1311b which is pressed by an anvil member 1312b connected to a threaded member 1313b pressing the expandable members 1311b in two directions perpendicular to the length axis of the elongated member 1310b for fixating the artificial acetabulum surface to the femoral bone 7.

Figure 17B:
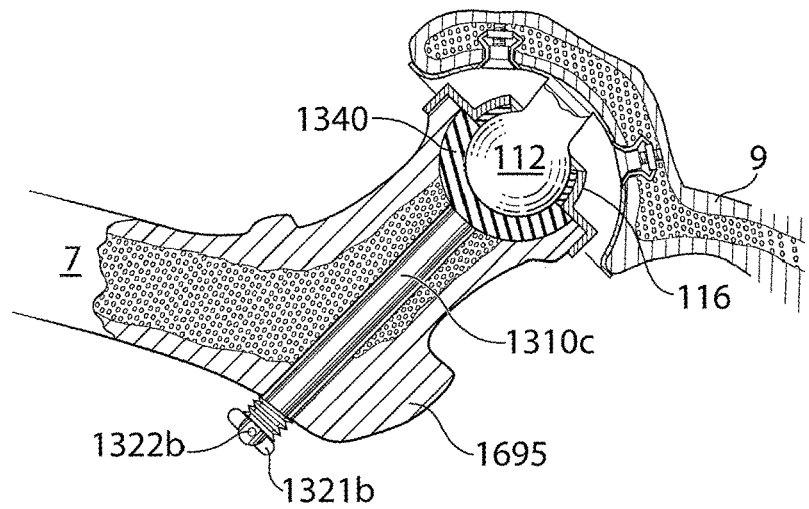
FIG. 17b shows an embodiment similar to the embodiment shown in FIG. 17a with the difference that the artificial acetabulum surface is fixated using an elongated member.

FIG. 17b shows an embodiment similar to the embodiment shown in FIG. 17a with the difference that the artificial acetabulum surface is fixated using an elongated member 1310c which penetrates the cancellous bone of the collum femur and the cortical bone of the femoral bone in the area of the greater trochanter 1695. The elongated member comprises a movable locking portion 1321b, pivotally arranged at a pivot point 1322b. The movable locking portion 1321b could change from a first to a second state around the pivot point 1322b. When the movable locking portion 1321b is placed in the second state it locks the elongated member on the outside of the femoral bone 7 in the area of the greater trochanter 1695.

Figure 17C:
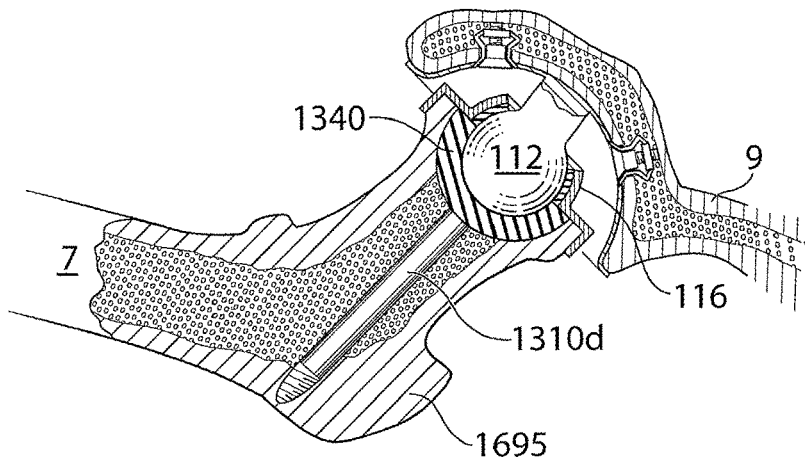
FIG. 17c shows an embodiment similar to the embodiment shown in FIG. 17a with the difference that the artificial acetabulum surface is fixated using an elongated member.

FIG. 17c shows an embodiment similar to the embodiment shown in FIG. 17a with the difference that the artificial acetabulum surface is fixated using an elongated member 1310d which penetrates the cancellous bone of the collum femur and enters the cortical bone of the femoral bone in the area of the greater trochanter 1695 but never exits the bone but rather is fixated inside of the bone 7.

Figure 18A:
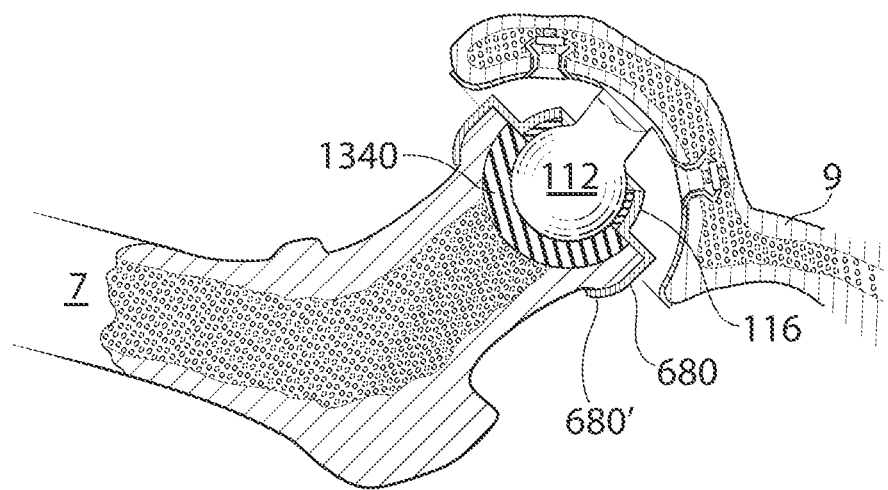
FIG. 18a shows an embodiment where the artificial acetabulum is fixated to the femoral bone using fixating portions.

FIG. 18a shows an embodiment where the artificial acetabulum 1340 is fixated to the femoral bone 7 using fixating portions 680 being part of the locking member 116. The fixating portions 680 comprises portions 680' clasping the surgically cut femoral bone and thereby fixating the artificial acetabulum surface to the femoral bone.

Figure 18B:
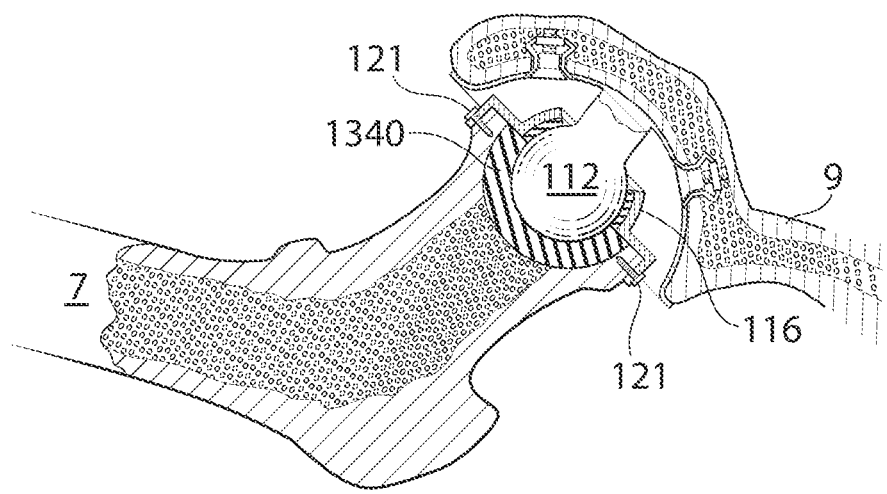
FIG. 18b shows an embodiment similar to the embodiment described with reference to FIG. 18a with the difference that the locking member is fixated to the surgically cut caput femur using screws.

FIG. 18b shows an embodiment similar to the embodiment described with reference to FIG. 18a with the difference that the locking member is fixated to the surgically cut caput femur using screws 121.

Figure 19:
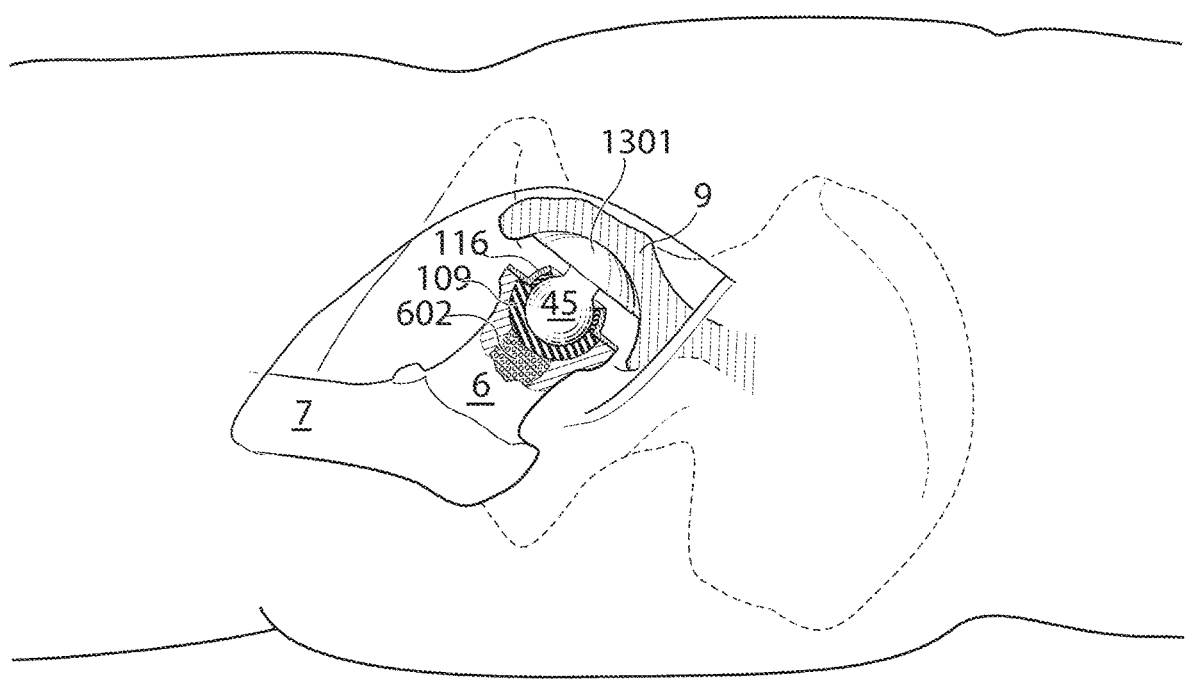
FIG. 19 shows the hip joint in section when the medical device is assembled and in its functional position in the hip joint.

FIG. 19 shows the hip joint in section when the medical device is assembled and in its functional position in the hip joint. The artificial caput femur surface 45 or convex hip joint surface 112 is fixated to the fixation part 1301, which in turn is fixated to the acetabulum 8, The locking member 116 locks the artificial convex caput femur surface 45 in the artificial concave acetabulum surface in the caput 5 and collum femur 6.

Figure 20:
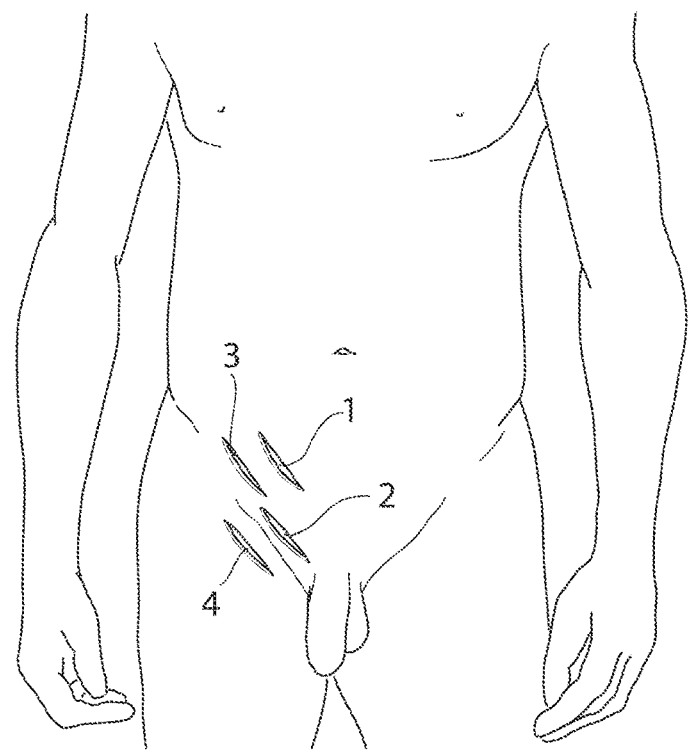
FIG. 20 shows a frontal view of a human patient when an incision for reaching an area of the hip joint through the pelvic bone in a surgical method has been performed.

FIG. 20 shows a frontal view of a human patient when an incision for reaching an area of the hip joint through the pelvic bone in a surgical method has been performed. According to one embodiment the incision 1 is made in the abdominal wall of the human patient. The incision 1 passes through the abdominal wall, preferably rectus abdominis and peritoneum, in to the abdomen of the human patent. In a second embodiment the incision 2 is conducted through the rectus abdominis and in to the pelvic area, below peritoneum. According to a third embodiment the incision 3 is performed just between Illium and the surrounding tissue, an incision 3 which could enable the pelvic bone to be dissected with very little penetration of fascia and muscular tissue. According to a fourth embodiment the incision 4 is made in the inguinal channel. In all of the four embodiments the tissue surrounding the pelvic bone 9 in the area opposite to acetabulum is removed or penetrated which enables the surgeon to reach the pelvic bone 9. It is obvious that the methods described may both be combined or altered reaching the same goal to dissect the pelvic bone on the opposite side of the acetabulum.

Figure 21:
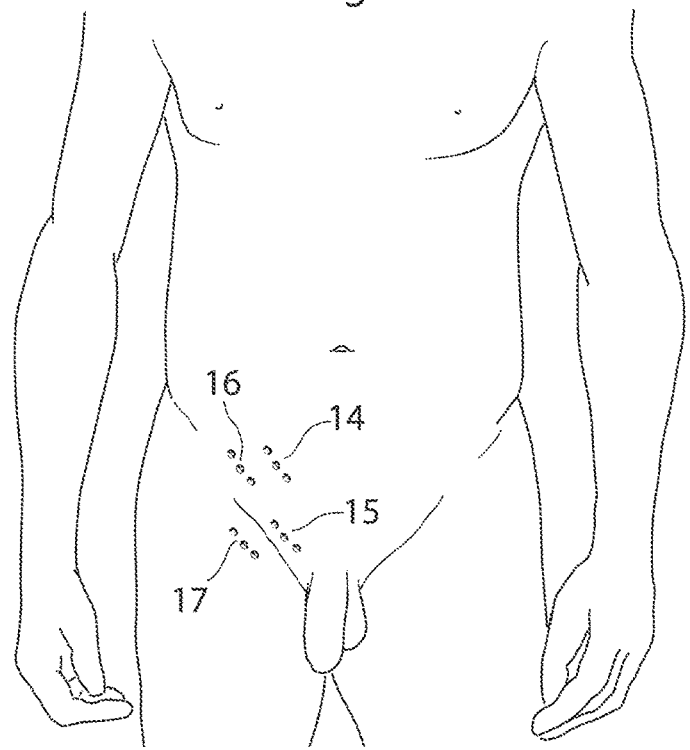
FIG. 21 shows a frontal view of a human patient when small incisions for reaching an area of the hip joint through the pelvic bone in a arthroscopic method has been performed.

FIG. 21 shows a frontal view of a human patient when small incisions for reaching an area of the hip joint through the pelvic bone in a arthroscopic method has been performed. According to a first embodiment the incisions 14 is made in the abdominal wall of the human patient. The small incisions enable the surgeon to insert arthroscopic trocars into the abdomen of the human patient. According to the first embodiment the incisions 14 passes through the abdomen, preferably rectus abdominis and peritoneum, in to the abdomen of the human patent. According to a second embodiment the small incisions 15 is conducted through the rectus abdominis and in to the pelvic area, below peritoneum. According to a third embodiment the small incisions 16 is performed just between Illium and the surrounding tissue, an incision 16 which could enable the pelvic bone to be dissected with very little penetration of fascia and muscular tissue. According to a fourth embodiment the incision 17 is made in the inguinal channel. In all of the four embodiments the tissue surrounding the pelvic bone 9 in the area opposite to acetabulum 8 is removed or penetrated which enables the surgeon to reach the pelvic bone 9.

Figure 22:
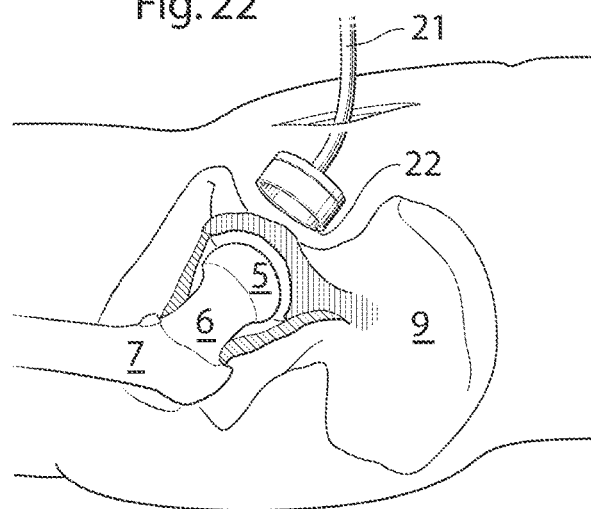
FIG. 22 shows the human patient in section when a medical device for creating a hole in the pelvic bone.

FIG. 22 shows the human patient in section when a medical device for creating a hole 18 in the pelvic bone 9 is inserted through an incision according to any of the embodiments described above. An elongated member 21, which could comprise a part or section adapted to be bent transfers force from an operating device (not shown) to the bone contacting organ 22. The bone contacting organ 22 is placed in contact with the pelvic bone 9 and creates a hole through a drilling, sawing or milling process powered by a rotating, vibrating or oscillating force distributed from the elongated member 21.

Figure 23:
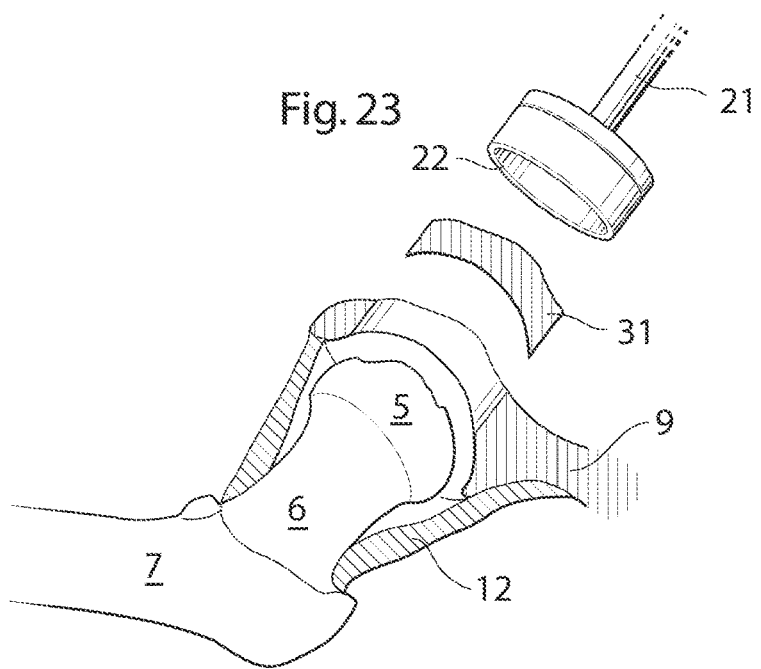
FIG. 23 shows the hip joint in section after the medical device for creating a hole in the pelvic bone has created said hole.

FIG. 23 shows the hip joint in section after the medical device for creating a hole 18 in the pelvic bone 9 has created said hole 18. According to this embodiment the hole 18 is created through the removal of a bone plug 31, however it is equally conceivable that said medical device comprises a bone contacting organ 22 adapted to create small pieces of bone, in which case the medical device could further comprise a system for transport of said small pieces of bone.

Figure 24:
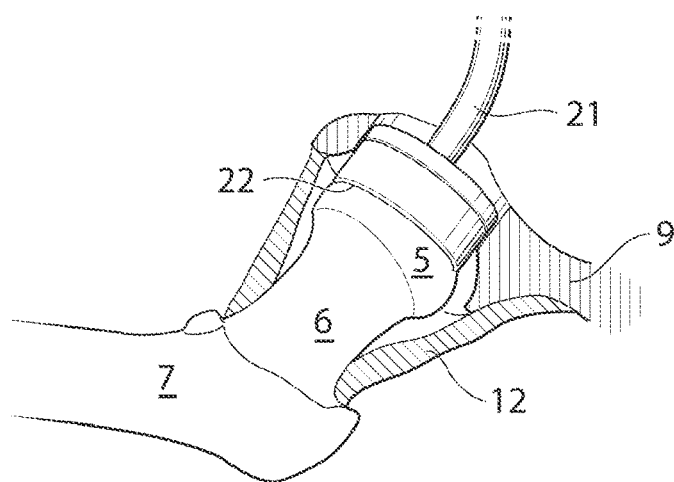
FIG. 24 shows how the medical device adapted to create a hole is inserted into the hip joint and placed in contact with the caput femur.

FIG. 24 shows how the medical device adapted to create a hole is inserted into the hip joint and placed in contact with the caput femur 5. According to this embodiment the medical device for creating a hole in the pelvic bone 9 and surgically cutting the caput femur 5 is the same medical device, however it is equally conceivable that there is a second medical device particularly adapted to surgically cut the caput femur 5.

Figure 25:
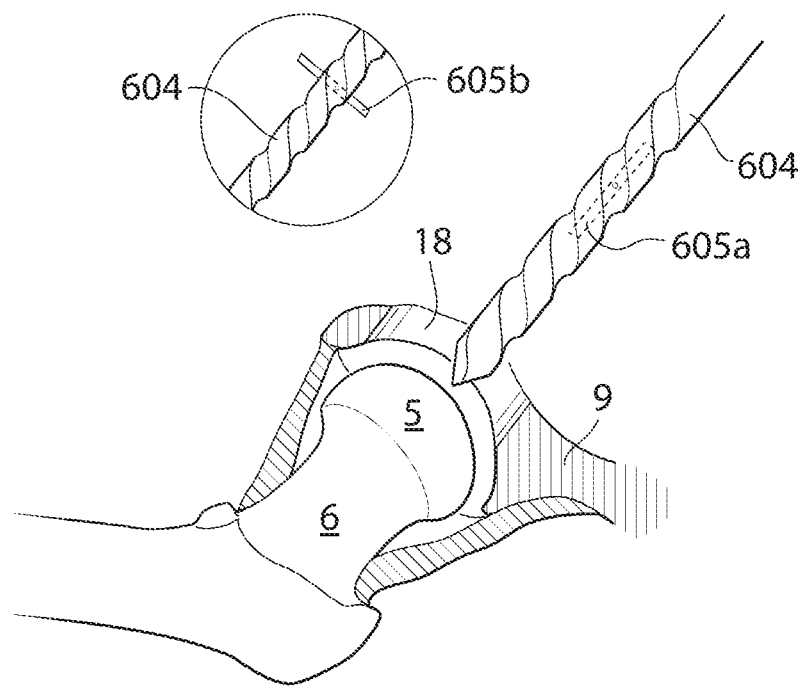
FIG. 25 shows the hip joint in section when a second medical device surgically removes the most proximal portion of the caput femur.

FIG. 25 shows the hip joint in section when a second medical device 604 surgically removes the most proximal portion of the caput femur 5. The second medical device 604 comprises a drilling portion in which a cutting member in a folded position 605a is placed.

Figure 26:
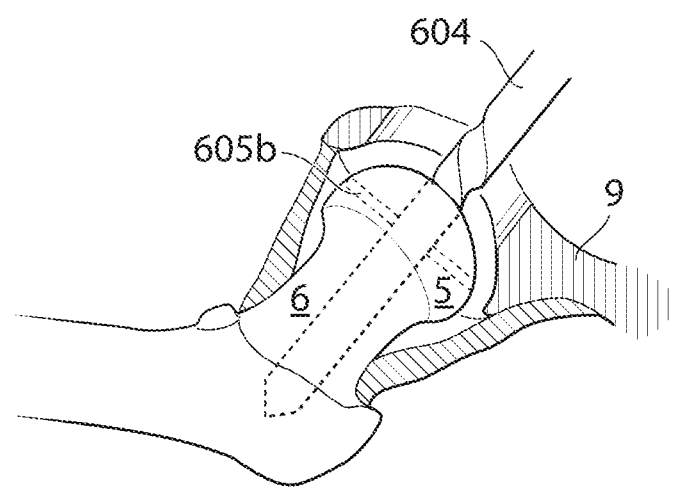
FIG. 26 shows the second medical device when the drilling portion is positioned inside of the femoral bone.

FIG. 26 shows the second medical device 604 when the drilling portion is positioned inside of the femoral bone, and the cutting member is placed in a cutting position 605b for cutting the proximal portion of the caput femur 5.

FIG. 23 shows the caput femur 5 after the proximal part has been removed along the section created by the medical device for creating a hole. The removing of the proximal part of the caput femur 5 create a surface of a section 102 in the cortical bone of the caput femur 5. A reamer 40 adapted to create a concave surface 103 in the caput femur 5 is applied to the elongated member 21 through a connecting section 101. According to this embodiment the elongated member 21 is the same as the elongated member used for the medical device adapted to create a hole in the pelvic bone 9, however it is equally conceivable that the elongated member 21 is specifically designed to enable the reaming of the caput femur 5. The reaming in the caput femur and part of the collum femur 6 is mainly performed in the cancellous bone, however that does not exclude the possibility the some of the reaming needs to be performed in the cortical bone of the caput femur 5 and/or the collum femur 6.

FIG. 17 shows the step of applying an adhesive 106 to the concave surface created by the reamer 40. The adhesive 106 is applied by an injecting member 104 comprising an injecting nozzle 105. The adhesive 106 is preferably a biocompatible adhesive such as bone cement. The injecting member 104 is in this embodiment adapted for introduction through a hole 18 in the pelvic bone 9, through the injecting member 104 being bent.

FIG. 18 shows the step of providing a medical device 109 comprising an artificial concave hip joint surface 110. The artificial concave hip joint surface 110 is fixated to the concave surface 103 created in the caput femur 5 and collum femur 6. The medical device 109 comprises a fixation support 111 adapted to anchor said artificial concave hip joint surface 110, to at least one of the caput femur 5 and the collum femur 6. The medical device 109 is adapted to be introduced to the hip joint through a hole 18 in the pelvic bone 9 using a inserting member 107. According to this embodiment the inserting member is bent and thereby adapted to operate through a hole 18 in the pelvic bone 9. The inserting member 107 comprises a connecting member 108 which is adapted to connect to the medical device 109. According to one embodiment the medical device 109 comprises a self lubricating material such as PTFE, however it is also conceivable that said medical device comprises: titanium, stainless steel, Corian, PE, or other acrylic polymers, in which case the medical device could be adapted to be lubricated after insertion in the hip joint.

Figure 27:
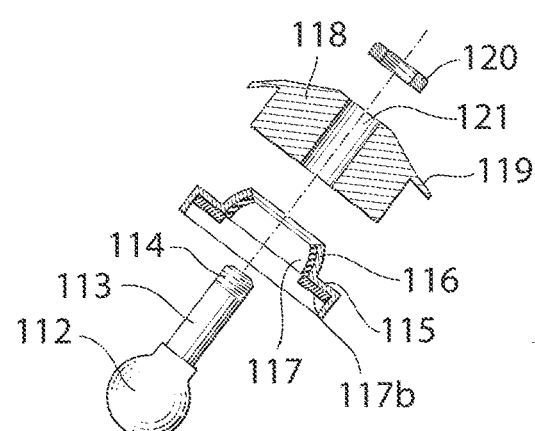
FIG. 27 shows a medical device comprising an artificial convex hip joint surface.

FIG. 27 shows a medical device comprising an artificial convex hip joint surface 112. The artificial convex hip joint surface 112 is adapted to be fixated to the pelvic bone 9, and is adapted to be inserted through a hole 18 in the pelvic bone 9. The medical device comprises a nut 120, comprising threads for securely fixating the medical device to the pelvic bone 9. The medical device further comprises a prosthetic part 118 adapted to occupy the hole 18 created in the pelvic bone 9 after the medical device has been implanted in the patient. The prosthetic part 118 comprises supporting members 119 adapted to be in contact with the pelvic bone 9 and assist in the carrying of the load placed on the medical device from the weight of the human patient in normal use. Normal use is defined as the same as a person would use a natural hip joint. Further the medical device comprises a locking member 116 comprising a surface 117 adapted to be in contact with the artificial convex hip joint surface 112. The locking member 116 further comprises fixating members 115 which are adapted to assist in the fixation of the locking member 116 to the caput femur 5 or collum femur 6, which in turns fixates the artificial convex hip joint surface 112. The artificial convex hip joint surface 112 is fixated to an attachment rod 113 comprising a thread 114 that corresponds to the thread of the nut 120 in connection with the prosthetic part 118.

Figure 28:
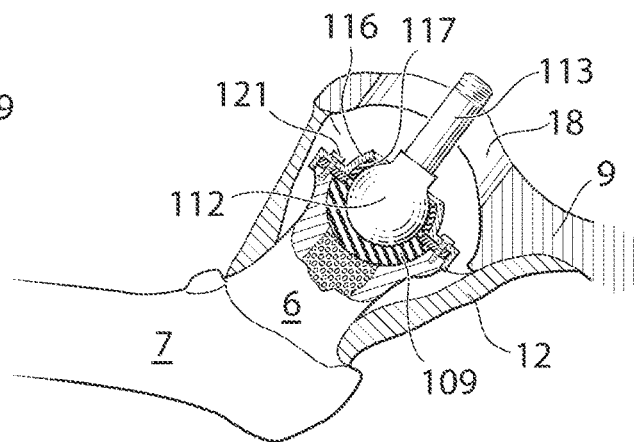
FIG. 28 shows the hip joint in section when the artificial convex hip joint surface is fixated in the medical device.

FIG. 28 shows the hip joint in section when the artificial convex hip joint surface is fixated in the medical device 109 comprising a concave hip joint surface 110. The convex hip joint surface 112 is secured in place by the locking member 116 which is fixated to the caput femur using screws 121. The surface of the locking member 117 and the concave hip joint surface 117 is placed in connection with the convex hip joint surface and could be made of a friction reducing material such as PTFE or a self lubricating powder material. However it is also conceivable that the connecting surfaces are lubricated using an implantable lubrication system adapted to lubricate the medical device after said medical device has been implanted in the human patient.

Figure 29:
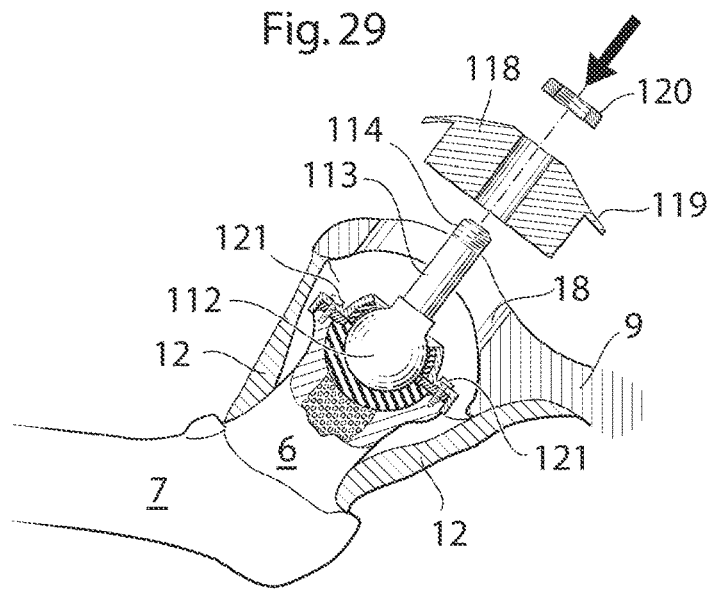
FIG. 29 shows the placing of a prosthetic part adapted to occupy the hole created in the pelvic bone.

FIG. 29 shows the placing of a prosthetic part 118 adapted to occupy the hole 18 created in the pelvic bone 9. The prosthetic part 118 comprises supporting members 119 adapted to be in contact with the pelvic bone 9 and assist in the carrying of the load placed on the medical device from the weight of the human patient. According to the embodiment shown in FIG. 12 the supporting members 119 are located on the abdominal side of the pelvic bone 9, however it is equally conceivable the supporting members 119 are located on the acetabulum side of the pelvic bone 9, in which case they are preferably displaceable for allowing insertion of the prosthetic part 118 through the hole 18 in the pelvic bone 9. Furthermore FIG. 12 shows the fixation of a nut 120 to the attachment rod 113. According to the embodiment shown in FIG. 12 the hole 18 in the pelvic bone 9 is adapted to be larger than the medical device allowing the medical device to be inserted in its full functional size. According to other embodiments the hole 18 is smaller in which case the medical device could comprise of several parts adapted to be connected after insertion in the hip joint, or the medical device could be expandable for insertion through a hole smaller than the full functional size of the medical device. The expandable medical device could be enabled through the elements of the medical device comprising elastic material.

Figure 30:
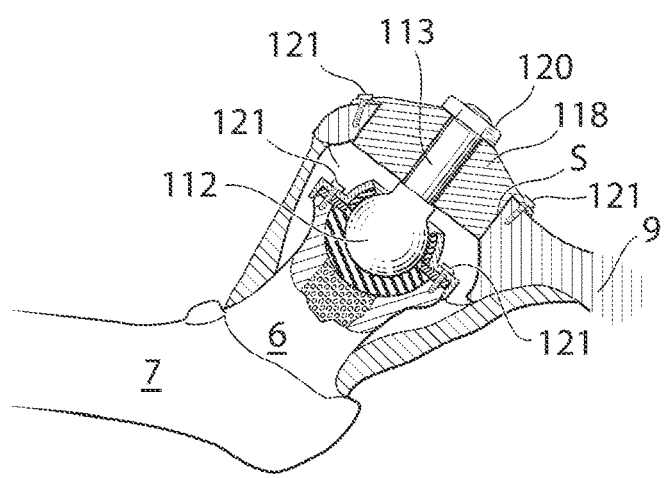
FIG. 30 shows the hip joint in section when all the elements of the medical device has been fixated in the area of the hip joint or its surroundings.

FIG. 30 shows the hip joint in section when all the elements of the medical device has been fixated in the area of the hip joint or its surroundings. The prosthetic part 113 adapted to occupy the hole 18 in the pelvic bone 9 is here fixated with screws 121, however these screws 121 could be assisted or replaced by an adhesive which could be applied to the surface S between the prosthetic part and the pelvic bone 9.

FIG. 31 shows the hip joint in section when the method of supplying the medical device is conducted according to another embodiment. The proximal part of the caput femur has been removed along the section created by the medical device for creating a hole. A reaming member 40 adapted to create a concave surface 103 in the caput femur 5 is here applied to a elongated member 206 which is inserted through a hole 205 going from the lateral side of the thigh, penetrating the cortical bone of the femoral bone 7 propagating along a length axis of the collum femur in the cancellous bone and entering the area of the hip joint. The elongated member 206 is operated using an operating device 207 which could be an electrically powered operating device, a hydraulically powered operating device or a pneumatically powered operating device. The reaming in the caput femur and part of the collum femur 6 is mainly performed in the cancellous bone, however that does not exclude the possibility the some of the reaming needs to be performed in the cortical bone of the caput femur 5 or the collum femur 6.

FIG. 32 shows the step of applying an adhesive 106 to the concave surface created by the reamer 40. The adhesive 106 is applied by an injecting member 104 comprising an injecting nozzle 105. The adhesive 106 is preferably a biocompatible adhesive such as bone cement. The injecting member 104 is in this embodiment adapted for introduction through a hole 18 in the pelvic bone 9, through the injecting member 104 being bent.

FIG. 33 shows the step of providing a medical device 109 comprising an artificial concave hip joint surface 110. The medical device is according to this embodiment provided with a hole positioned in the length axis of the collum femur 6. The medical device is through the hole adapted to be guided by the elongated member 206 or a guiding rod placed in the hole 205 along a length axis of the collum femur 6. Inserting the medical device into the hip joint while the elongated member 206 or guiding rod runs through the hole of the medical device facilitates the positioning of the medical device and ensures the different parts of the medical device is centered for functioning as a unit. In the embodiment shown in FIG. 33 the medical device 109 is inserted into the hip joint as a single unit, however it is equally conceivable that the medical device 109 is inserted in parts (not shown) which are then connected to form the medical device after implantation in the patient. The artificial concave hip joint surface 110 is fixated to the concave surface 103 created in the caput femur 5 and collum femur 6. The medical device 109 comprises a fixation support 111 adapted to anchor said artificial concave hip joint surface 110, to at least one of the caput femur 5 and the collum femur 6. The medical device 109 is adapted to be introduced to the hip joint through a hole 18 in the pelvic bone 9 using a manipulation device 122 comprising a gripping member 123. According to this embodiment the manipulation device 122 is bent and thereby adapted to operate through a hole 18 in the pelvic bone 9. According to one embodiment the medical device 109 comprises a self lubricating material such as PTFE, however it is also conceivable that said medical device comprises: titanium, stainless steel, Corian, PE, or other acrylic polymers, in which case the medical device could be adapted to be lubricated after insertion in the hip joint.

Figure 34:
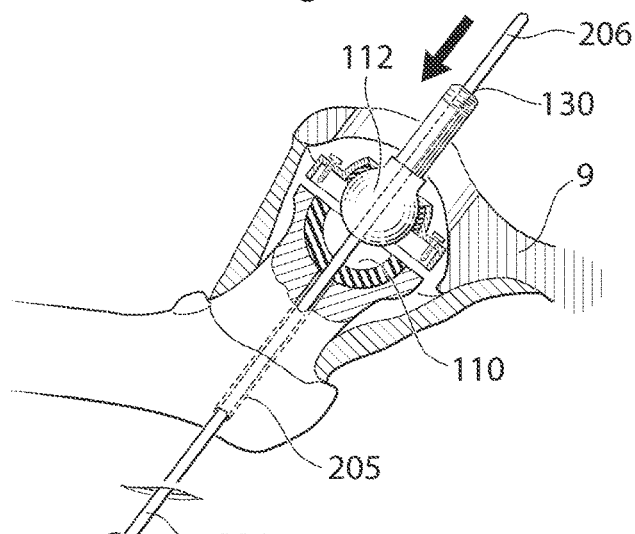
FIG. 34 shows the hip joint in section when the artificial convex hip joint surface is fixated in the medical device comprising a concave hip joint surface.

FIG. 34 shows the hip joint in section when the artificial convex hip joint surface is fixated in the medical device 109 comprising a concave hip joint surface 110, the medical device is guided using the elongated member 206 or a guiding rod. The convex hip joint surface 112 is secured in place by the locking member 116 which is fixated to the caput femur using screws 121, the convex hip joint surface is guided using the elongated member 206 or a guiding rod. The surface of the locking member 117 and the concave hip joint surface 110 is placed in connection with the convex hip joint surface and could be made of a friction reducing material such as PTFE or a self lubricating powder material. However it is also conceivable that the connecting surfaces are lubricated using an implantable lubrication system adapted to lubricate the medical device after said medical device has been implanted in the human patient. The elongated member or guiding rod 206 can be adapted to act as a centering rod for centering the at least one artificial hip joint surface inside of the hip joint. According to the embodiment shown the elongated member 206 is inserted through the femoral bone, however according to other embodiments, not shown, the elongated member is positioned inside of the hip joint from the acetabulum side.

Figure 35:
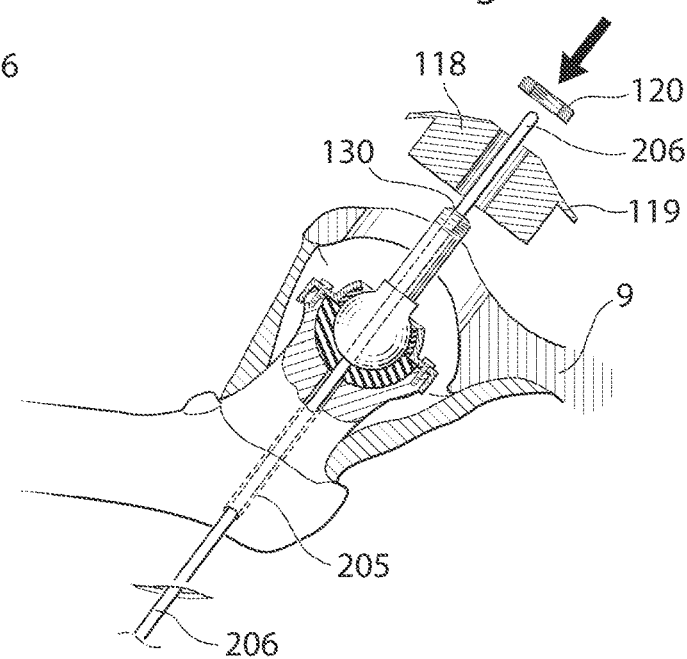
FIG. 35 shows the placing of a prosthetic part adapted to occupy the hole created in the pelvic bone.

FIG. 35 shows the placing of a prosthetic part 118 adapted to occupy the hole 18 created in the pelvic bone 9. The prosthetic part 118 comprises supporting members 119 adapted to be in contact with the pelvic bone 9 and assist in the carrying of the load placed on the medical device from the weight of the human patient. Furthermore FIG. 35 shows the fixation of a nut 120 to the attachment rod 113, which in turn is guided by the elongated member 206 or a guiding rod.

Figure 36:
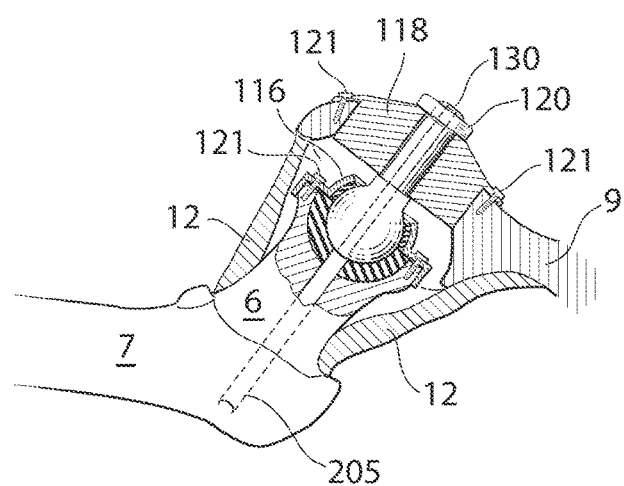
FIG. 36 shows the hip joint in section when all the elements of the medical device has been fixated in the area of the hip joint or its surroundings.

FIG. 36 shows the hip joint in section when all the elements of the medical device has been fixated in the area of the hip joint or its surroundings. The prosthetic part 118 adapted to occupy the hole 18 in the pelvic bone 9 is here fixated with screws 121, however these screws 121 could be assisted or replaced by an adhesive which could be applied to the surface S between the prosthetic part and the pelvic bone 9. The elongated member 206 or guiding rod has been retracted through the incision in the thigh.

Figure 37:
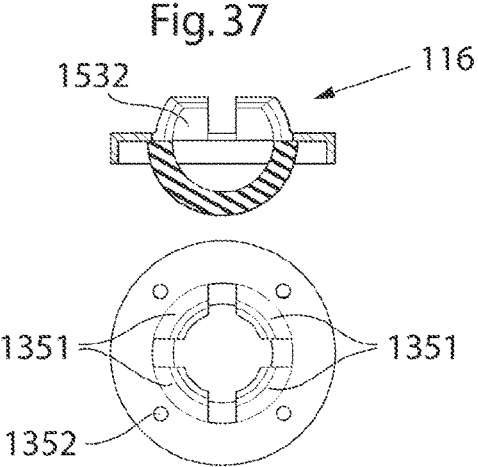
FIG. 37 shows an embodiment of a locking member.

FIG. 37 shows an embodiment of a locking member 116, wherein the locking member 116 comprises a surface adapted to be in contact with the artificial convex hip joint surface 1353, the locking member 116 is adapted to, in a first state, lock the artificial caput femur 112 to the artificial acetabulum surface 1340, and in a second state, release said artificial caput femur 112 from said artificial acetabulum 1340. The locking member 116 is adapted to change from the first to the second state when a predetermined amount of strain is placed on the locking member 116. The locking member 116 according to the embodiment shown in FIG. 37, comprises four elastic portions 1351, and the locking member 116 is adapted to change from the first to the second state using the elasticity of the elastic portions 1351. The locking member 116 is adapted to be fixated to the femoral bone 7 using screws adapted to be placed in holes 1352 adapted therefor.

Figure 38:
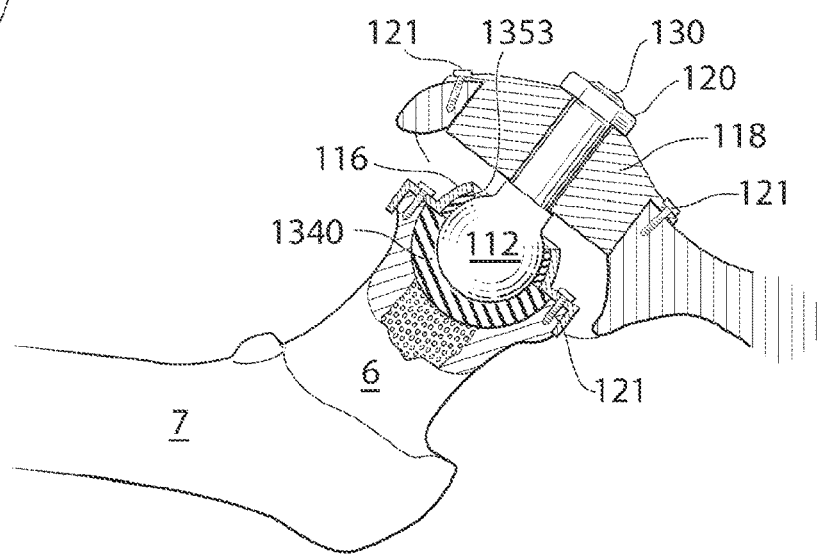
FIG. 38 shows the hip joint in section when a two state locking member locks the artificial caput femur in the artificial acetabulum.

FIG. 38 shows the hip joint in section when a two state locking member 116 locks the artificial caput femur 112 in the artificial acetabulum 1340. The two state locking member 116 is fixated to the femoral bone 7 using screws 121, and is here shown in its first state in which the locking member 116 locks the artificial caput femur 112 to the artificial acetabulum 1340.

Figure 39:
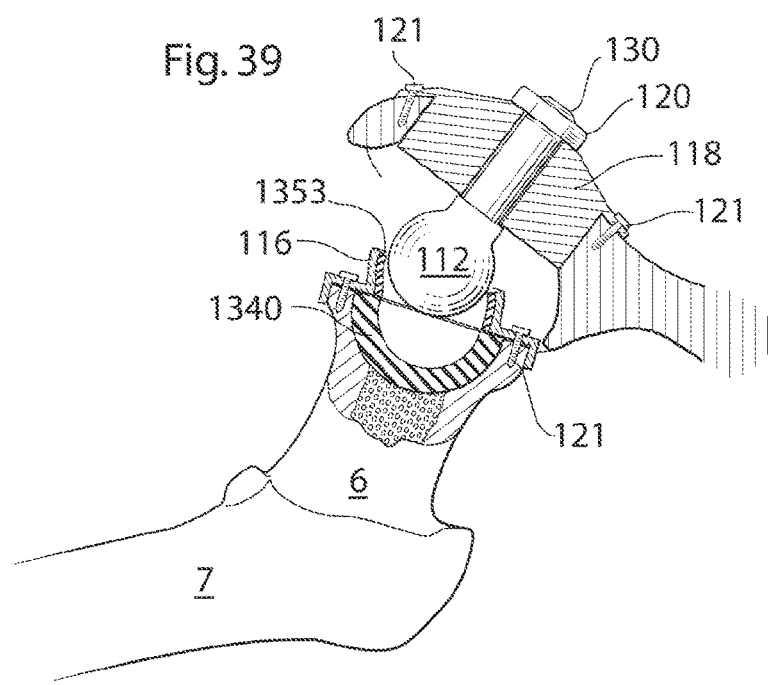
FIG. 39 shows the hip joint in section according to the embodiment of FIG. 38, but when the two state locking member is in its second state.

FIG. 39 shows the hip joint in section according to the embodiment of FIG. 38, but when the two state locking member 116 is in its second state, in which the locking ring 116 releases the artificial caput femur 112 from the artificial acetabulum surface 1340. The construction with the releasing locking ring 116 reduces the risk of strain placed on the artificial joint injuring the fixation points, i.e. the contact with bone; it further enables the artificial joint to be non-invasively relocated in case of luxation.

According to the above mentioned embodiments the medical device is adapted to be inserted through a hole in the pelvic bone, however it is equally conceivable that the medical device according to any of the embodiment above is adapted to be inserted through a hole in the hip joint capsule or the femoral bone of the human patient.

Please note that any embodiment or part of embodiment as well as any method or part of method could be combined in any way. All examples herein should be seen as part of the general description and therefore possible to combine in any way in general terms.

The invention claimed is:

1. A medical device for implantation in a hip joint of a human patient, the natural hip joint having a ball shaped caput femur as the proximal part of the femoral bone with a convex hip joint surface towards the centre of the hip joint and a bowl shaped acetabulum as part of the pelvic bone with a concave hip joint surface towards the centre of the hip joint, the medical device comprising; an artificial caput femur, comprising a convex surface towards the centre of the hip joint, wherein said artificial convex caput femur is adapted to, when implanted:
   be fixated to the pelvic bone of the human patient, and
   be in movable connection with an artificial acetabulum surface fixated to the femoral bone of the patient, thereby forming a ball and socket joint,
   wherein the medical device further comprises a fixation element comprising a fixation surface adapted to be in contact with the surface of the acetabulum and adapted to fixate the artificial convex caput femur to at least the acetabulum of the pelvic bone, characterized in that said fixation surface is at least one of:
   comprising at least one hole adapted to receive a mechanical fixation element, and
   adapted to fixate said medical device to the pelvic bone using an adhesive placed between said fixation surface and said surface of the acetabulum, when said device is implanted in the hip joint.

2. The medical device according to claim 1, wherein said fixation element comprises an elongated member, and wherein said elongated member is adapted to:
   a. be inserted through a hole in the pelvic bone, such that said elongated member is partially placed at least one of:
      i. inside of the pelvic bone, and
      ii. on the abdominal side of the pelvic bone, and
   b. adapted to be structurally changed inside of the pelvic bone or on the abdominal side of the pelvic bone, such that said elongated member fixates the fixation element to the pelvic bone contacting the pelvic bone on the inside or abdominal side thereof, when implanted.

3. The medical device according to claim 2, wherein said elongated member comprises an expandable portion, wherein said expandable portion is adapted to:
   c. in a first, non-expanded state, be inserted through the hole in the pelvic bone, substantially along a length axis of said elongated member,
   d. expand at least in one direction further to said length axis, such that said elongated member is placed in an expanded state, which fixates the fixation element to the pelvic bone, on the inside or abdominal side thereof.

4. The medical device according to claim 3, wherein said expandable portion comprises two or more expanding elements in connection with an anvil member, wherein said anvil member is adapted to press on the expanding elements following an action performed from the acetabulum side of the pelvic bone, such that said two or more expanding elements expands in at least one direction substantially perpendicular to the length axis of the elongated member.

5. The medical device according to claim 3, wherein said expandable portion of said elongated member is adapted to expand at least in one direction away from said length axis, when a rotational movement is performed from the acetabulum side of the pelvic bone, when said device is implanted.

6. The medical device according to claim 3, wherein said anvil member is in connection with a threaded member extending substantially along the length axis of the elongated member, and wherein said medical device further comprises a corresponding threaded part, and wherein said action performed from the acetabulum side of the pelvic bone comprises rotating said corresponding threaded part such that said threaded member is pulled in the direction of the acetabulum side of the pelvic bone, which by the connection with the anvil member presses said two or more expanding elements.

7. The medical device according to claim 2, wherein said elongated member comprises a movable locking portion adapted to have a first and second state, wherein said movable locking portion, in said first state is adapted to be inserted into a hole in the pelvic bone, and in said second state is adapted to hinder the elongated member from passing through said hole in the pelvic bone by said movable locking portion contacting the surface of the pelvic bone on the abdominal side thereof.

8. The medical device according to claim 7, wherein said movable locking portion is pivotally arranged to said elongated member.

9. The medical device according to claim 1, wherein the artificial convex caput femur comprises a threaded part adapted to engage a corresponding threaded member, and wherein said artificial convex caput femur is adapted to be further fixated to the pelvic bone by a relative rotating movement of the artificial convex caput femur in relation to said threaded part.

10. The medical device according to claim 1, wherein said fixation surface comprises at least one hole adapted to receive a mechanical fixation element, and wherein said fixation element further comprises an elongated member adapted to be placed in said hole, wherein said elongated member is further adapted to:
  be inserted through a hole in the pelvic bone, such that said elongated member is partially placed on the abdominal side of the pelvic bone, and
  be structurally changed on the abdominal side of the pelvic bone, such that said elongated member fixates the fixation element to the pelvic bone.

11. The medical device according to claim 1, further comprising an artificial acetabulum surface, comprising a concave surface towards the centre of the hip joint, adapted to, when implanted, be fixated to the femoral bone of the human patient, and be in movable connection with the artificial caput femur surface fixated to the pelvic bone of the patient.

12. The medical device according to claim 11, wherein said medical device further comprises a fixation element comprising a fixation surface adapted to be in contact with the surface of the caput femur or collum femur, wherein said fixation element is adapted to fixate the artificial concave acetabulum to the femoral bone.

13. The medical device according to claim 11, further comprising an elongated member comprising an expandable portion adapted to:
  in a first, non-expanded state, be inserted through a hole in the femoral bone, substantially along a length axis of the elongated member, and
  expand at least in one direction away from said length axis, such that said elongated member is placed in an expanded state, which fixates the fixation element to the femoral bone, from the inside thereof.

14. The medical device according to claim 11, wherein said artificial acetabulum surface comprises at least one beyond part adapted to pass beyond the equator of the artificial caput femur, clasping said artificial caput femur for fixating said artificial caput femur in said artificial acetabulum surface.

15. A medical device for implantation in a hip joint of a human patient, the natural hip joint having a ball shaped caput femur as the proximal part of the femoral bone with a convex hip joint surface towards the centre of the hip joint and a bowl shaped acetabulum as part of the pelvic bone with a concave hip joint surface towards the centre of the hip joint, the medical device comprising; an artificial caput femur, comprising a convex surface towards the centre of the hip joint, wherein said artificial convex caput femur is adapted to, when implanted:
  be fixated to the pelvic bone of the human patient, and
  be in movable connection with an artificial acetabulum surface fixated to the femoral bone of the patient, thereby forming a ball and socket joint,
wherein the medical device further comprises a fixation element comprising a fixation surface adapted to be in contact with the surface of the acetabulum and adapted to fixate the artificial convex caput femur to at least the acetabulum of the pelvic bone, characterized in that said fixation element comprises an elongated member adapted to:
  a. be inserted through a hole in the pelvic bone, such that said elongated member is partially placed at least one of:
    i. inside of the pelvic bone, and
    ii. on the abdominal side of the pelvic bone, and
  b. adapted to be structurally changed inside of the pelvic bone or on the abdominal side of the pelvic bone, such that said elongated member fixates the fixation element to the pelvic bone contacting the pelvic bone on the inside or abdominal side thereof, when implanted.

16. A medical device for implantation in a hip joint of a human patient, the natural hip joint having a ball shaped caput femur as the proximal part of the femoral bone with a convex hip joint surface towards the centre of the hip joint and a bowl shaped acetabulum as part of the pelvic bone with a concave hip joint surface towards the centre of the hip joint, the medical device comprising; an artificial caput femur, comprising a convex surface towards the centre of the hip joint, wherein said artificial convex caput femur is adapted to, when implanted:
  be fixated to the pelvic bone of the human patient, and
  be in movable connection with an artificial acetabulum surface fixated to the femoral bone of the patient, thereby forming a ball and socket joint,
wherein the medical device further comprises
  a fixation element comprising a fixation surface adapted to be in contact with the surface of the acetabulum and adapted to fixate the artificial convex caput femur to at least the acetabulum of the pelvic bone,
  an artificial acetabulum surface, comprising a concave surface towards the centre of the hip joint, adapted to, when implanted, be fixated to the femoral bone of the human patient, and be in movable connection with the artificial caput femur surface fixated to the pelvic bone of the patient, and
  an elongated member comprising an expandable portion adapted to:
    in a first, non-expanded state, be inserted through a hole in the femoral bone, substantially along a length axis of the elongated member, and
    expand at least in one direction away from said length axis, such that said elongated member is placed in an expanded state, which fixates the fixation element to the femoral bone, from the inside thereof.

* * * * *